(12) United States Patent
Chabot et al.

(10) Patent No.: US 6,358,687 B1
(45) Date of Patent: Mar. 19, 2002

(54) METHODS FOR MONITORING THE BINDING OF A1/UP1 TO SINGLE-STRANDED NUCLEIC ACID SEQUENCES, AND TO MEASURE THE EFFECT OF THIS BINDING ON TELOMERE EXTENSION AND PROTECTION

(75) Inventors: Benoit Chabot; Raymund Wellinger, both of Sherbrooke (CA)

(73) Assignee: Telogene Inc., Fleurimont (CA)

( * ) Notice: Subject to any disclaimer, the term of this patent is extended or adjusted under 35 U.S.C. 154(b) by 0 days.

(21) Appl. No.: 09/536,259

(22) Filed: Mar. 27, 2000

(30) Foreign Application Priority Data

Mar. 25, 1999 (CA) ............................................. 2264262

(51) Int. Cl.[7] ............................ C12Q 1/68; C12P 19/34
(52) U.S. Cl. ........................ 435/6; 435/91.1; 435/91.2; 435/4
(58) Field of Search .......................... 435/6, 91.1, 91.2, 435/4

(56) References Cited

U.S. PATENT DOCUMENTS 5,217,864 A * 6/1993 Heintz et al. ................... 435/6
5,733,730 A * 3/1998 De Lange ...................... 435/6

OTHER PUBLICATIONS

Matsuo et al. International Journal of Oncology. 9:1201–1205, 1996.*
L. Hayflick et al.; "The Serial Cultivation of Human Diploid Cell Strains"; *Experimental Cell Research*; 1961; pp. 585–621.
Richard McElligott, et al.; "The terminal DNA structure of mammalian chromosomes"; *The EMBO Journal*; vol. 16, No. 12; 1997; pp. 3705–3714.

Carol W. Greider, "Telomere Length Regulation"; *Annu. Rev. Biochem.*; 1996; pp. 337–365.
Fritz Muller, et al.; "New Telomere Formation after Developmentally Regulated Chromosomal Breakage during the Proces of Chromatin Diminution in *Ascaris lumbriciodes*"; *Cell*; Nov. 15, 1991; vol. 67, pp. 815–822.
Guo–Liang Yu, et al.; "Developmentally programmed Healing of Chromosomes by Telomerse in tetrahymena"; *Cell*; Nov. 15, 1991; vol. 67, pp. 823–832.
John T. Gray, et al.; "Cloning and Expression of Genes for the Oxytricha Telomere–Binding Protein: Specific Subunit Interactions in the Telomeric Complex"; *Cell*; Nov. 15, 1991; vol. 67, pp. 807–814.
Titia de Lange; "Telomere Dynamics and Genome Instability in Human Cancer"; *Telomeres*; 1995; pp. 265–293.
Michelle S. Rhyu; "Telomeres, Telomerase, and Immortality"; *Journal of the National Cancer Institute*; Jun. 21, 1995; vol. 87, No. 12, pp. 884–894.
Carol W. Greider, et al.; "Telomeres and Telomerase in Cell Senescence and Immortalization"; *Cellular Aging and Cell Death*; 1996; pp. 123–138.
Lisa L. Sandell, et al.; "Loss of a Yeast Telomere: Arrest, Recovery, and Chromosome Loss"; *Cell*; Nov. 19, 1993; vol. 75, pp. 729–739.

(List continued on next page.)

*Primary Examiner*—Carla J. Myers
(74) *Attorney, Agent, or Firm*—Merchant & Gould P.C.

(57) ABSTRACT

The present invention relates to the length of telomeres and to their effect on proliferation and senescence in cells. More specifically, it concerns the ability of hnRNP A1 and its shortened derivative UP1 to alter the length of telomeres in cells. More precisely, the invention relates to the ability of A1/UP1 to bind telomerase RNA, to bind and to protect mammalian telomeric DNA, and to modulate telomere extension and replication. Finally, the present invention relates to agents which can interfere with the binding of A1/UP1 to telomeres and telomerase, and to the use of protection, extension and replication assays to measure the biological impact of these agents.

15 Claims, 19 Drawing Sheets

OTHER PUBLICATIONS

Christopher M. Counter, et al.; "telomere shortening associated with chromosome instability is arrested in immortal cells which express telomerase activity"; *The EMBO Journal*; 1992; vol. 11, No. 5, pp. 1921–1929.

E. H. Blackburn; "Telomerases"; *Annu. Rev. Biochem.*; 1991; pp. 113–129.

Samuel Goldstein; ; "Replicative Senescence: The Human Fibroblast Comes of Age"; *Science*; Sep. 7, 1990; pp. 1129–1133.

Jerry W. Shay, et al.; "Quantitation of the Frequency of Immortalization of Normal Human Diploid Fibroblasts by SV40 Large T–Antigen"; *Experimental Cell Research 184*; 1989; pp. 109–118.

Calvin B. Harley, et al.; "Telomeres shorten during ageing of human fibroblasts"; *Nature*; May 31, 1990; Vo. 345, pp. 458–460.

Richard C. Allsopp, et al.; "Telomere length predicts replicative capacity of human fibroblasts"; *Proc. Natl. Acad. Sci. USA*; Nov. 1992; vol. 89, pp. 10114–10118.

Titia de Lange; "Activation of telomerase in a human tumor"; *Proc. Natl. Acad. Sci. USA*; Apr. 1994; vol. 91, pp. 2882–2885.

S. Riva, et al.; "Mammalian single–stranded DNA binding protein UP I is derived from te hnRNP core protein A1"; *The EMBO Journal*; 1986; vol. 5, No. 9, pp. 2267–2273.

Phillip M. Reveal, et al.; "Synthesis of the Mammalian Telomere Lagging Strand in Vitro"; *The Journal of Biological Chemistry*; 1997; vol. 272, No. 18, pp. 11678–11681.

Christopher G. Burd, et al.; "RNA binding specificity of hnRNP A1: significance of hnRNP A1 high–affinity binding sites in pre–mRNA splicing"; *The EMBO Journal*, 1994; vol. 13, No. 5, pp. 11979–1204.

Jianzhong Ding, et al.; "Crystal structure of the two–RRM domain of hnRNP A1 (UP1) complexed with single–stranded telomeric DNA"; *Genes & Development*; 1999; pp. 1102–1115.

Carolyn M. Price, et al.; "DNA Recognition and Binding by the Euplotes Telomere Protein"; *Biochemistry*; 1992; pp. 10835–10843.

Carolyn M. Price; "Telomere Structure in *Euplotes crassus*: Characterizaton of DNA–Protein Interactions and Isolation of a Telomere Binding Protein"; *Molecular and Cellular Biology*; 1990; pp. 3421–3431.

Jack D. Griffith, et al.; "Mammalian Telomeres End in a Large Duplex Loop"; *Cell*; May 14, 1999; vol. 97, pp. 503–514.

John Prescott, et al.; "Functionally interacting telomerase RNAs in the Yeast telomerase complex"; *Genes & Development*; 1997; pp. 2790–2800.

Marco Blanchette, et al.; "Modulation of exon skipping by high–affinity hnRNP Al–binding sites and by intron elements that repress splice site utilization"; *The EMBO Journal*; 1999; vol. 18, No. 7, pp. 1939–1952.

Akila Mayeda, et al.; "Function of conserved domains of hnRNP A1 and other hnRNP A/B proteins"; *The EMBO Journal*; 1994; vol. 13, No. 22, pp. 5483–5495.

Guowei Fang, et al.; "Telomere Proteins"; *Telomeres*; 1995; pp. 69–105.

Stacie J. Froelich–Ammon, et al., "Modulation of telomerase activity by telomere DNA–binding proteins in Oxytricha"; *Genes & Development*; 1998; pp. 1504–1514.

Stephen D. Johnston, et al.; "Gbp1p, a Protein with RNA Recognition Motifs, Binds Single–Stranded Telomeric DNA and Changes Its Binding Specificity upon Dimerization"; *Molecular and Cellular Biology*; Jan. 1999; pp. 923–933.

Leena Gandhi, et al.; "Interaction of recombinant Tetrahymena telomerase proteins p80 and p95 with telomerase RNA and telomeric DNA substrates"; *Genes & Development*, 1998; pp. 721–733.

Constance I. Nugent, et al.; "Cdc13p: A Single–Strand Telomeric DNA–Binding Protein with a Dual Role in Yeast Elomere Maintenance"; *Science*Oct. 11, 1996; vol. 274, pp. 249–252.

Valerie Virta–Pearlman, et al.; "Est1 has the properties of a single–stranded telomere end–binding protein"; *Genes & Development*1996; pp. 3094–3104.

Barbara R. Steiner, et al.; "Association of the Est1 protein with telomerase activity in yeast"; *Proc. Natl. Acad. Sci. USA*; Apr. 1996; vol. 93, pp. 2817–2821.

Victoria Lundblad, et al.; "Telomerase and telomerase: A Simple Picture Becomes Complex"; *Cell*; Nov. 1, 1996; vol. 87, pp. 369–375.

Paul S. Miller, et al.; "Oligonucleotide Inhibitors of Gene Ecxpression in Living Cells: New Opportunities in Drug Design"; *Annual Reports in Medicinal Chemistry*; 1988; pp. 295–304.

Francois Morvan, et al.; "α–DNA I. Synthesis, characterization by high field $^1$HNMR, and base–pairing properties of the unnatural hexadeoxyribonucleotide α–[d(CpCpTpTpCpC)] with its complement β–[d(GpGpApApGpG)]"; *Nucleic Acids Research*; 1986; vol. 14, No. 12, pp. 5019–5035.

D.Y. Kwoh, et al.; "Transcription–based amplification system and detection of amplified human immunodeficiency virus type 1 with a bead–bvased sandwich hybridization format"; *Proc. Natl. Acad. Sci. USA*; Feb. 1989; vol. 86, pp. 1173–1177.

Rick Weiss; "Hot Prospects for New Gene Amplifier"; *Science*; Nov. 29, 1991; pp. 1292–1293.

G. Terrance Walker, et al.; "Isothermal in vitro amplification of DNA by a restriction enzyme/DNA polymerase system"; *Proc. Natl. Acad. Sci. USA*; Jan. 1992; vol. 89, pp. 391–396.

G. Terrance Walker, et al.; "Strand displacement amplification–an isothermal, in vitro DNA amplification technique"; *Nucleic Acids research*; 1992; vol. 20, No. 7, pp. 1691–1696.

Sherie L. Morrison; "Transfectomas Provide Novel Chimeric Antibodies"; *Science*; vol. 229, pp. 1202–1207.

S. Fazekas DeSt. Groth et al.; "Production of Monoclonal Anti9bdies: Strategy and tractics"; *Journal of Immunological Methods*; 1980; pp. 1–21.

Woodring E. Wright, et al.; "Experimental elongation of telomerase extends the lifespan of immortal x normal cell hybrids"; *The EMBO Journal*; 1996; vol. 15, No. 7, pp. 1734–1741.

Junli Feng, et al.; "The RNA Component of Human Telomerase"; *Science*; Sep. 1, 1995; vol. 269, pp. 1236–1241.

Toru M. Nakamura, et al.; "Telomerase Catalytic Subunit Homologs from Fission Yeast and Human"; *Science*; Aug. 15, 1997; vol. 277, pp. 955–959.

Andrea G. Bodnar, et al.; "Extension of Life–Span by Introduction of Telomerase into Normal Human Cells"; *Science*; Jan. 16, 1998 vol. 279, pp. 349–.

David W. Stockton, et al.; "Telomerase prevents the accelerated cell ageing of Werner syndrome fibroblasts"; *Nature Genetics*; Jan. 2000, vol. 24, pp. 16–19.

Han–Woong Lee, et al.; "Essential role of mouse telomerase in highly proliferative organs"; *Nature*; Apr. 9, 1998; vol. 392, pp. 569–574.

Hiroyuki Niida, et al.; "Severe growth defect in mouse cell lacking the telomerase RNA component"; *Nature Genetics*; Jun. 1998; vol. 19, pp. 203–206.

William C. Hahn, et al.; "Inhibition of telomerase limits the growth of human cancer cells"; *Nature Medicine*; Oct. 1999; vol. 5, No. 10, pp. 1164–1170.

B. S. Herbert, et al.; "Inhibition of human telomerase in immortal human cells leads to progresive telomere shortening and cell death"; *PNAS*; Dec. 7, 1999; vol. 96, No. 25, pp. 14276–14281.

Xiaoling Zhang, et al.; "Telomere shortening and apoptosis in telomerase–inhibited human tumor cells"; *Genes & Development*; 1999; pp. 2388–2399.

Bas van Steensel, et al.; "Control of telomere length by the human telomeric protein TRF 1"; *Nature*; Feb. 20, 1997; vol. 385, pp. 740–743.

Bas van steensel, et al.; "TRF2 Protects Human Telomerase from End–to–End Fusions"; *Cell*; Feb. 6, 1998; vol. 92, pp. 401–413.

Jan Karlseder, et al.; "p53–and ATM–Dependent Apoptosis Induced by Telomerase Lackin TRF2"; *Science*; Feb. 26, 1999; vol. 283, pp. 1321–1325.

Gideon Dreyfuss, et al.; "hnRNP Proteins and the Biogenesis of mRNA"; *Annu. Rev. Biochem.*; 1993; pp. 289–321.

Helene LaBranche, et al.; "Telomere elongation by hnRNP A1 and a derivative that interacts with telomeric repeats and telomerase"; *Nature Genetics*; Jun. 1998; vol. 19, pp. 199–202.

Carol W. Greider, et al.; "A telomeric sequence in the RNA of tetrahymena telomerase required for telomere repeat synthesis"; *Nature*; Jan. 26, 1989; vol. 337, pp. 331–337.

* cited by examiner

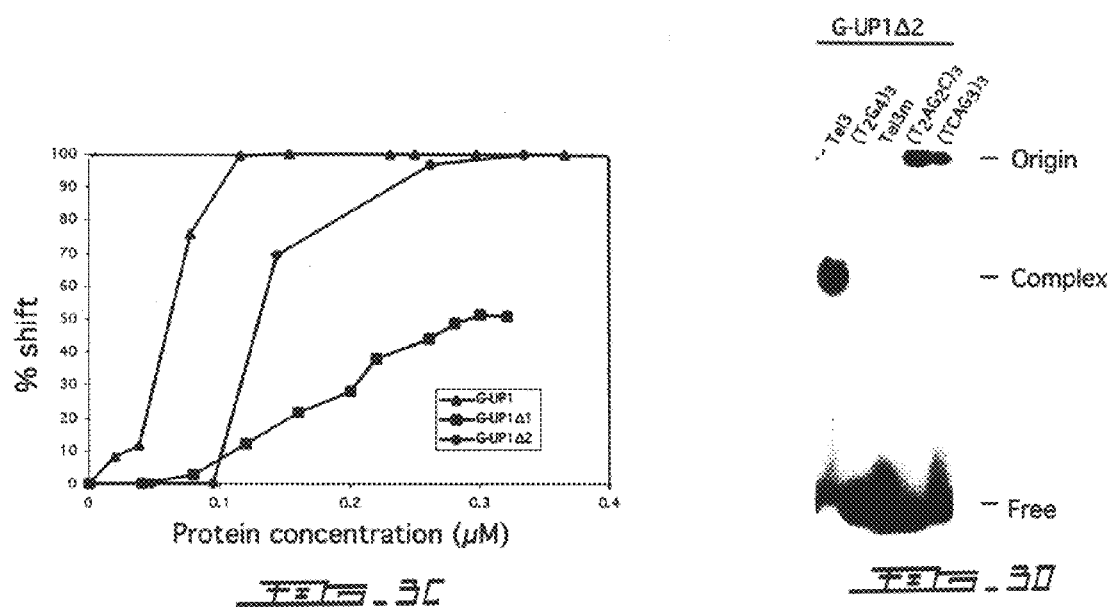

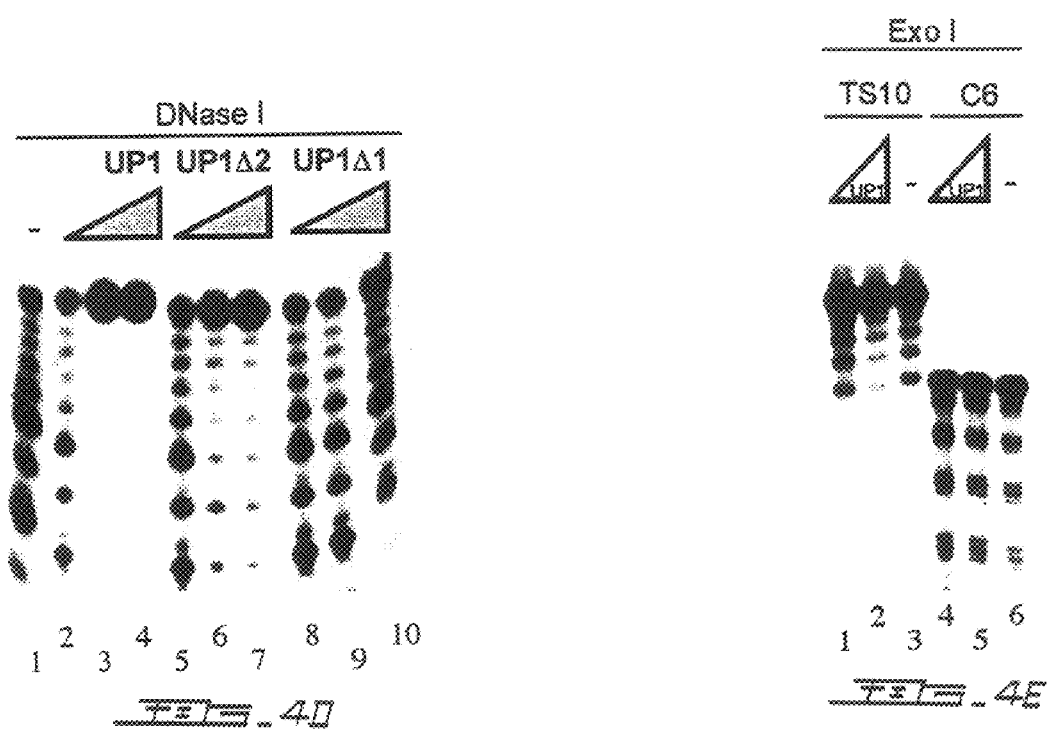

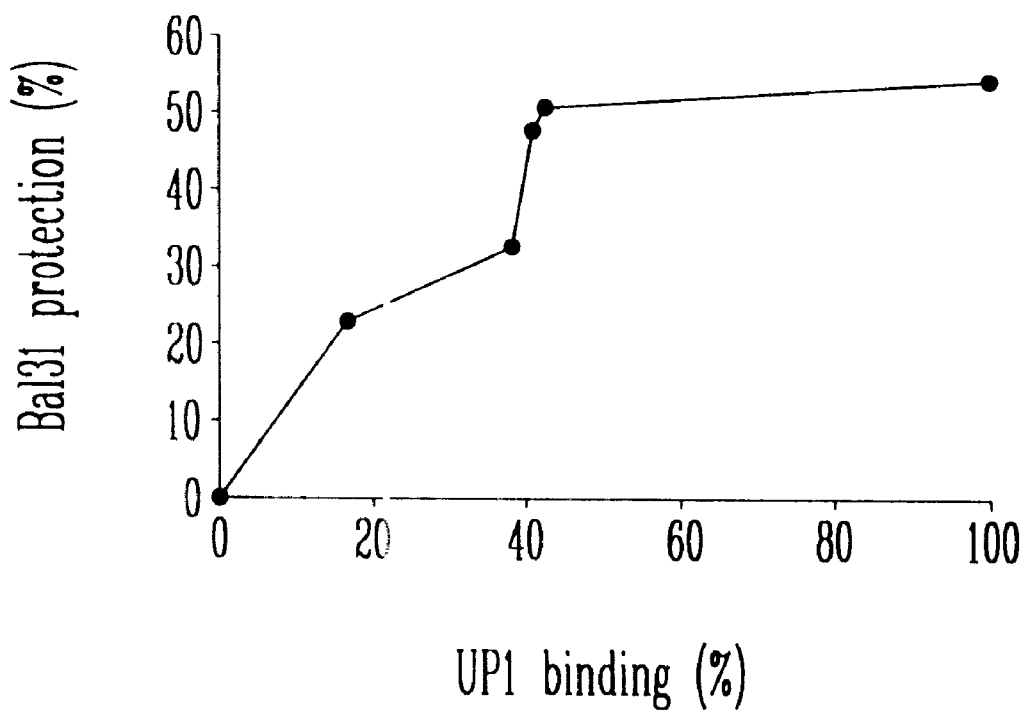
FIG._4F

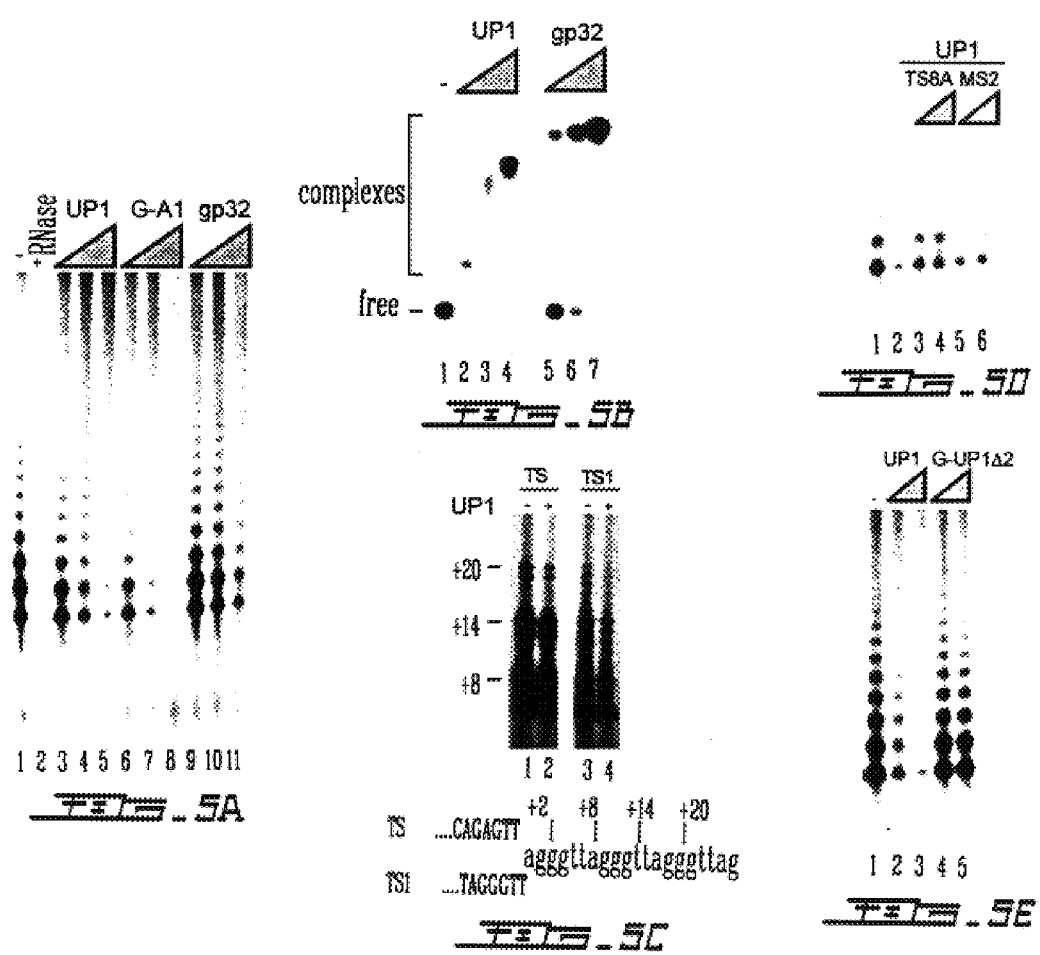

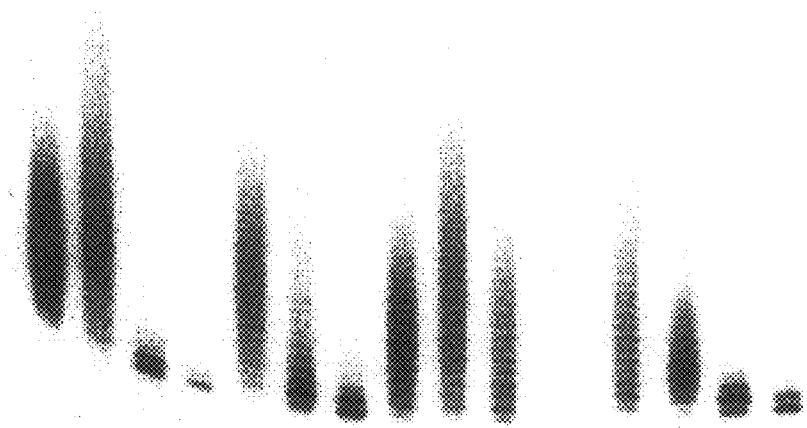

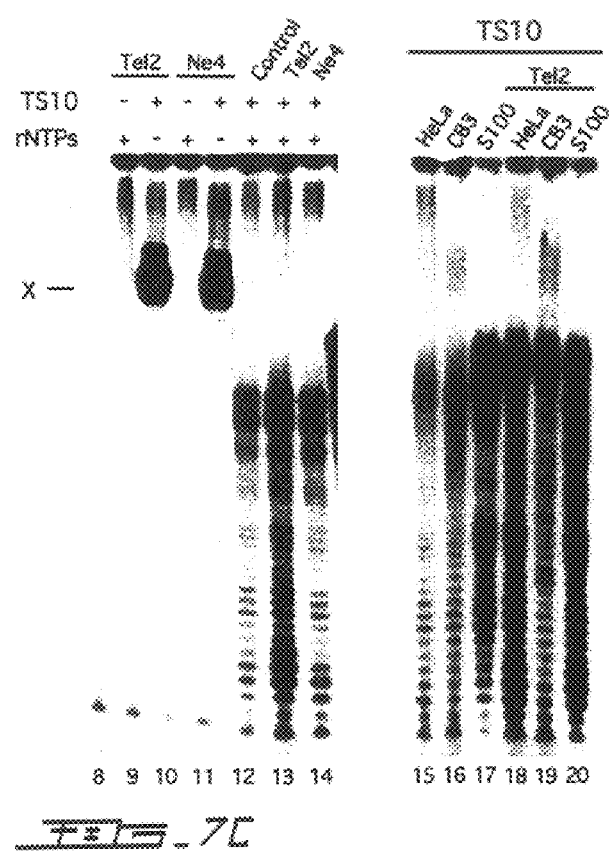
FIG. 7C

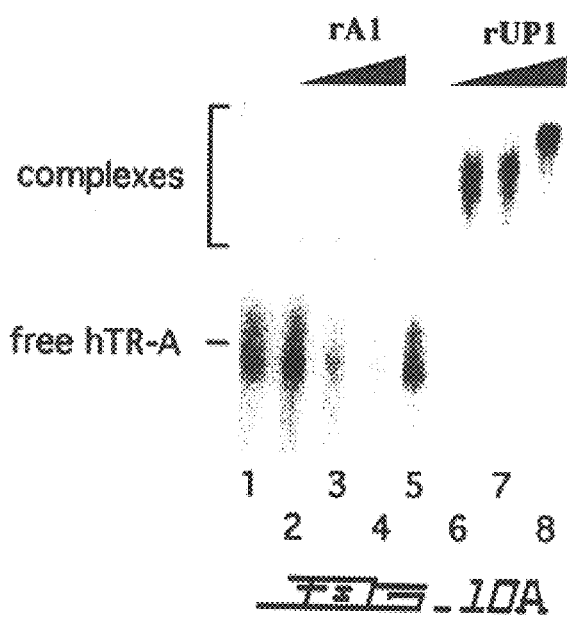
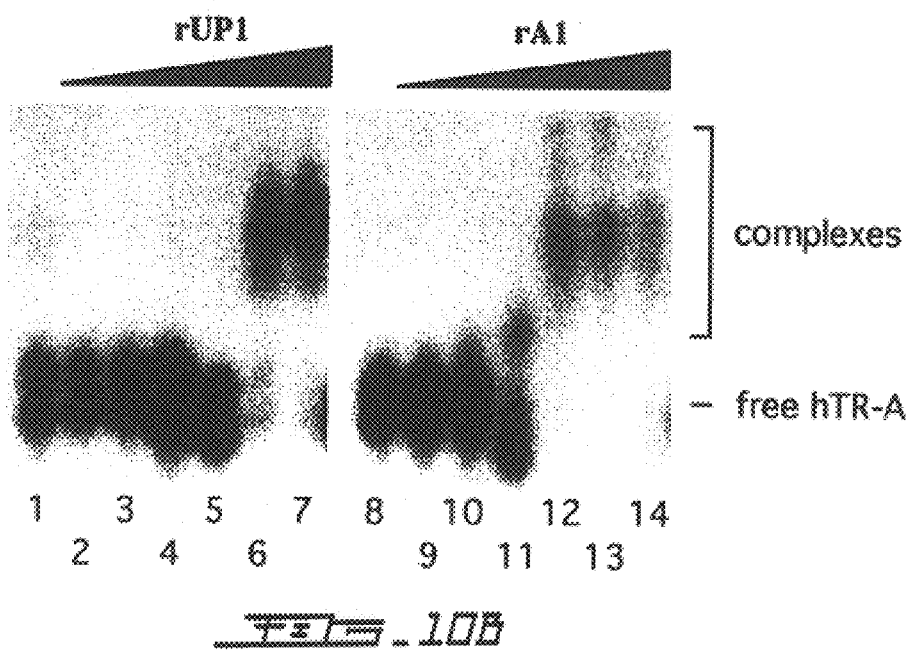

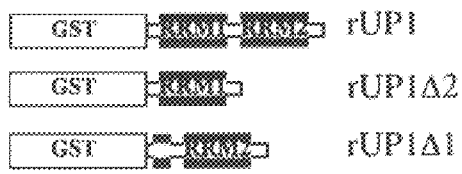
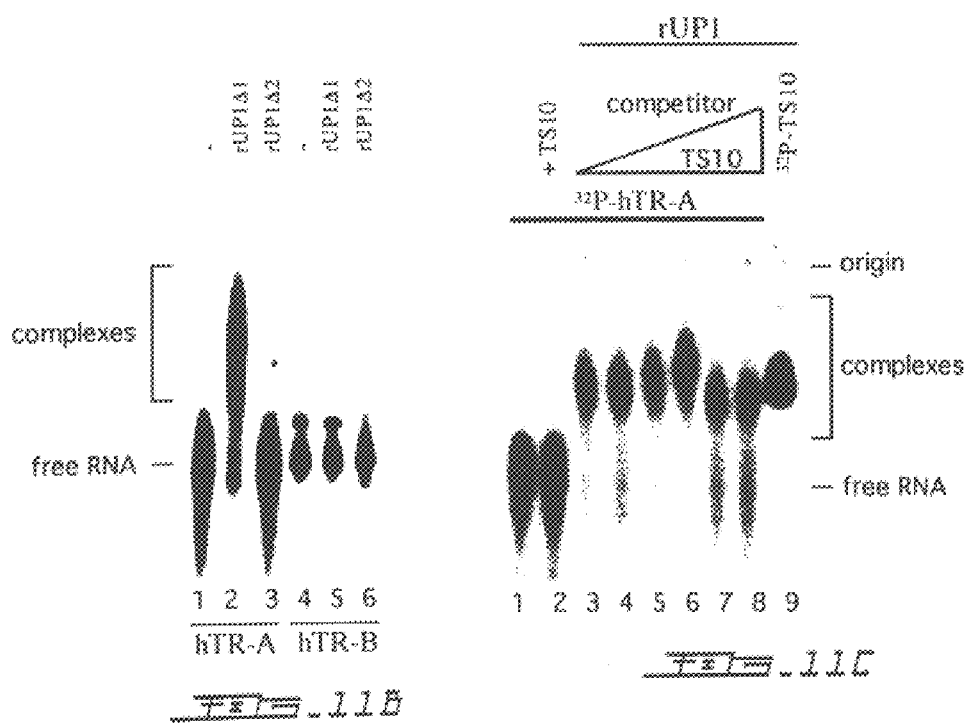

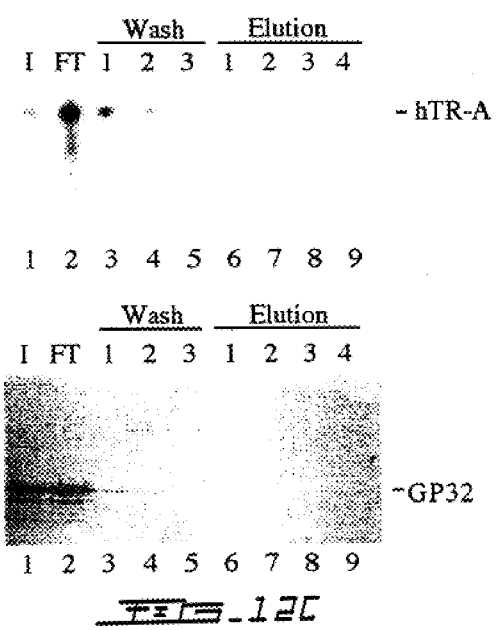
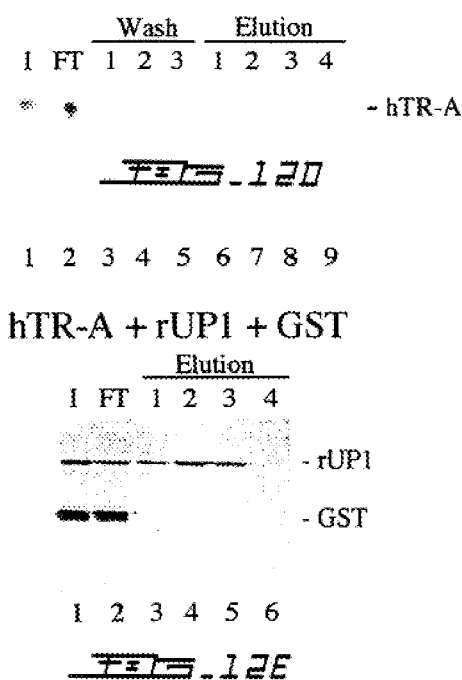

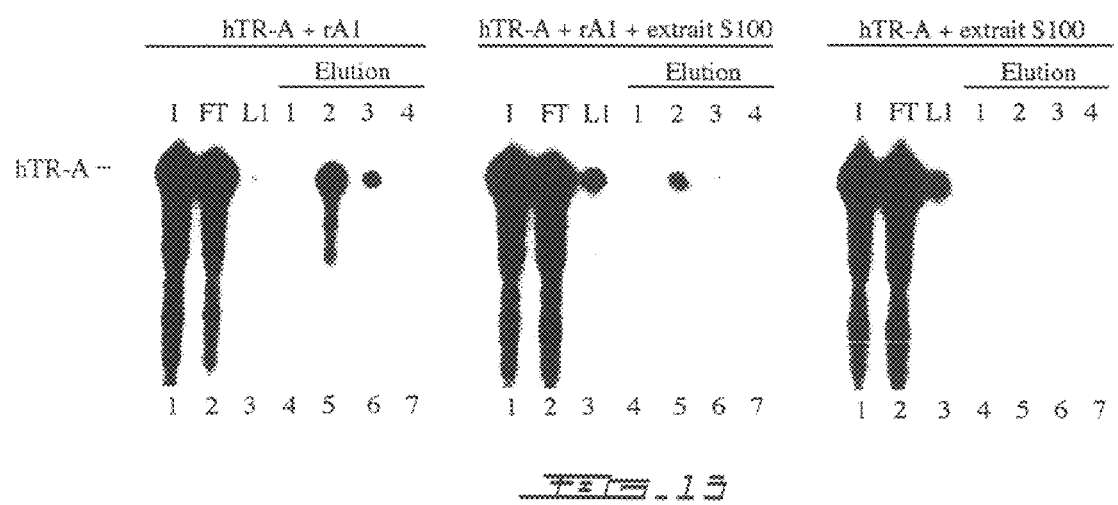

SEQUENCE LISTING

<160> NUMBER OF SEQ ID NOS: 18

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: oligonucleotide

<400> SEQUENCE: 1
ggcctagtgt cctggtaggg ttagggttag ggt           33

<210> SEQ ID NO 2
<211> LENGTH: 33
<212> TYPE: DNA
<213> ORGANISM: Artificial Sequence
<220> FEATURE:

```
<223> OTHER INFORMATION: Description of Artificial Sequence:
      oligonucleotide

<400> SEQUENCE: 2
tagggttagg gttagggtgg tcctgtgatc cgg                               33

<210> SEQ ID NO 3
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ccggatcaca ggacc                                                  15

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
ccaggacact aggcc                                                  15

<210> SEQ ID NO 5
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 5
ttagggttag ggttagggtt agggttaggg ttagggttag ggttagggtt agggttaggg   60

<210> SEQ ID NO 6
<211> LENGTH: 61
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
ttagggttag ggttagggtt agggttaggg ttagggttag ggttagggtg aagaaaatta   60
g                                                                  61

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
aatccgtcga gcagagtt                                                18

<210> SEQ ID NO 8
<211> LENGTH: 18
<212> TYPE: DNA
<213> ORGANISM: Artificial Sequence
```

```
<220> FEATURE:
<223> OTHER INFORMATION: Description of Artificial Sequence:
      oligonucleotide

<400> SEQUENCE: 8
aatccgtcga gtagggtt                                                      18

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
gggggtggga gcagggagg                                                     20

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
ccctaaccct aaccctaacc ctaaccctaa                                         30

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
ccctaaccct aaccctaacc ctaaccctaa ccctaa                                  36

<210> SEQ ID NO 12
<211> LENGTH: 34
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
cgaagtcgac tgcagcgtac cctgatggtg tacg                                    34

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 13
ggttagggtt agggttag                                                      18

<210> SEQ ID NO 14
<211> LENGTH: 24
<212> TYPE: DNA
<213> ORGANISM: Artificial Sequence
<220> FEATURE:
```

```
<223> OTHER INFORMATION: Description of Artificial Sequence:
      oligonucleotide

<400> SEQUENCE: 14
ggttagggtt agggttaggg ttag                                            24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 15
tttgggtttg ggtttgggtt tggg                                            24

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
tagggttagg gt                                                         12

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
tagggttagg gttagggt                                                   18

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
tagggttagg gttagggtta gggt                                            24
```

METHODS FOR MONITORING THE BINDING OF A1/UP1 TO SINGLE-STRANDED NUCLEIC ACID SEQUENCES, AND TO MEASURE THE EFFECT OF THIS BINDING ON TELOMERE EXTENSION AND PROTECTION

FIELD OF THE INVENTION

The present invention relates to the length of telomeres and to their effect on proliferation and senescence in cells. More specifically, it concerns the ability of hnRNP A1 and its shortened derivative UP1 to alter the length of telomeres in cells. More precisely, the invention relates to the ability of A1/UP1 to bind telomerase RNA, to bind and to protect mammalian telomeric DNA, and to modulate telomere extension and replication. Finally, the present invention relates to agents which can interfere with the binding of A1/UP1 to telomeres and telomerase, and to the use of protection, extension and replication assays to measure the biological impact of these agents.

BACKGROUND OF THE INVENTION

Telomeres are the DNA structure at the ends of the chromosomes of eukaryotes, including human, and are comprised of variable lengths of double-stranded repeats terminating with single-stranded G-rich repeats originally identified in yeast and protozoa (McElligot and Wellinger, 1997, EMBO J. 16:3705).

Review articles concerning telomeres include Greider, 1996, (Ann. Rev. Biochem. 65:337). Relevant articles on various aspects of telomeres include Muller et al., 1991, Cell 67:815; Yu et al., 1991, Cell 67:823; Gray et al., 1991, Cell 67:807; de Lange, 1995, "Telomere Dynamics and Genome Instability in Human Cancer", E. Blackburn and C. W. Greider (eds), in Telomeres, Cold Spring Harbor Laboratory Press, pp. 265–293; Rhyu, 1995, J. Nati. Cancer Inst. 87:884; Greider and Harley, 1996, "Telomeres and Telomerase in Cell Senescence and Immortalization", in Cellular Aging and Cell Death, Wiley-Liss, Inc., pp. 123–138. Thus, telomeres are involved in the maintenance of chromosome structure and function. Furthermore, it appears that loss of telomeric DNA activates cellular processes involved in the detection and control of DNA damage, and affects cellular proliferation and senescence.

Maintenance of the integrity of telomeres is essential for cell survival (Sandell et al., 1993, Cell 75:729–739). The proliferative potential of cells has been correlated with alterations in the length of these tandemly repeated sequences (Counter et al., 1992, EMBO J. 11:1921–1929). In addition, maintenance of telomere length and the regulation thereof are essential, pluripotent cellular functions as they are involved in the transmission of genetic information to daughter cells, senescence, cell growth and cancer (Blackburn, 1992, Annu. Rev. Biochem. 61:113–129).

The finite replicative capacity of normal human cells, e.g., fibroblasts, is characterized by a cessation of proliferation in spite of the presence of serum growth factors. This cessation of replication after a maximum of 50 to 100 population doublings in vitro is referred to as cellular senescence. See, Goldstein, 1990, Science 249:1129. The replicative life span of cells is inversely proportional to the in vivo age of the donor (Martin et al., 1979, Lab. Invest. 23:86) and is therefore suggested to reflect in vivo ageing on a cellular level.

Cellular immortalization (unlimited life span) may be thought of as an abnormal escape from cellular senescence. Normal human somatic cells appear to be mortal, i.e., have finite replication potential. In contrast, the germ line and malignant tumor cells are immortal (have indefinite proliferative potential). Human cells cultures in vitro appear to require the aid of transforming oncoproteins to become immortal and even then the frequency of immortalization is $10^{-6}$ to $10^{-7}$ (Shay et al., 1989, Exp. Cell Res. 184:109). A variety of hypotheses have been advanced over the years to explain the causes of cellular senescence. One such hypothesis proposes that the loss of telomeric DNA with age, eventually triggers cell cycle exit and cellular senescence (Harley et al. 1990, Nature (London) 345:458–460; Allsopp et al., 1992, Proc. Natl. Acad. Sci. USA 89:10114–10118; Counter et al., 1992, EMBO J. 11:1921–1929).

Human primary fibroblasts in culture enter crisis after a precise number of cell division associated with gradual telomere shortening, at which point all the cells die (de Lange, 1994, Proc. Natl. Acad. Sci. USA 91:2882–2885). Mouse primary fibroblasts have longer and/or more stable telomeres and display a similar behavior when cultured in vitro. However, after crisis, primary mouse cells in culture spontaneously immortalize with a frequency of $10^{-6}$, possibly because longer telomeres facilitate the growth of mutant cells (de Lange, 1994, Proc. Natl. Acad. Sci. USA 91:2882–2885).

It should be noted, as mentioned above, that other hypotheses have been advanced to explain senescence and that there is yet to be a consensus or a universally accepted hypothesis therefor. Previously, the causal relationship between telomeres and cancer/ageing/senescence had been built entirely on correlative studies.

Recent data has shown that telomeres play a direct role in cell senescence and transformation. Indeed, Wright et al., 1996, EMBO J. 15:1734–1741, using telomerase-negative cells which have limited life span in tissue culture, have shown that the introduction of oligonucleotides carrying telomeric repeats causes telomere elongation and increases the proliferative capacity of these cells. Moreover, the authors state that "previous studies had shown a remarkable correlation between telomere length and cellular senescence. The present results provide the first experimental evidence for a true causal relationship between telomere length and a limited proliferative capacity". Feng et al., 1995 (Science 269:1236–1241) showed that a human cell line (HeLa) transfected with an antisense telomerase RNA, looses telomeric DNA and begins to die after 23–26 cell doublings. The authors claim that "the results support the hypothesis that telomere loss leads to crisis and cell death once telomeres are shortened to a critical length".

The telomerase is part of a multi-component ribonucleoprotein complex. The RNA component of the human telomerase ribonucleoprotein has been identified. The catalytic protein subunit has recently been cloned (Nakamura et al., 1997, Science 277:955).

More recent advances have confirmed the role of telomeres in cell senescence. Overexpression of the catalytic protein component of telomerase can lead to telomere elongation and extension of the proliferative capacity of telomerase-negative fibroblasts in culture (Bodnar et al. 1998, Science 279:349). Overexpression of this protein also prevents the accelerated ageing of human fibroblasts derived from patients with Werner syndrome (Wyllie et al. 2000, Nat. Genet.). Mice and murine ES cells that do not express telomerase RNA show telomere shortening and become impaired in long-term viability (Lee et al. 1998, Nature 392:569; Niida et al. 1998, Nat. Genet. 19:203). Recent studies have also supported the role of telomeres in cellular transformation. The expression of a catalytically inactive form of telomerase or the inactivation of telomerase RNA in human immortal and cancer cell lines promotes telomere shortening, growth arrest and cell death (Hahn et al. 1999, Nat. Med. 5:1164; Herbert et al. 1999, Proc. Natl. Acad. Sci. USA 96:14276; Zhang et al. 1999, Genes Dev. 13:2388).

The length of telomeres and cell viability can also be affected by proteins that bind to vertebrate telomeres. TRF1 and TRF2 are proteins that bind to double-stranded telomeric repeats. Overexpression of TRF1 promotes telomere shortening (van Steensel and de Lange 1997, Nature 385:740). Expression of a dominant negative version of TRF2 promotes end-to-end fusion of chromosomes, an event which leads to p53-dependent cell death by apoptosis (van Steensel et al. 1998, Cell 92:401; Karlseder et al. 1999, Science 283:1321).

The postulated link between senescence/proliferation of cells and telomere length has led to therapeutic and diagnostic methods relating to telomere length or to telomerase, the ribonucleoprotein enzyme involved in the synthesis of telomeric DNA. PCT Publication No. 93/23572 describes oligonucleotide agents that either reduce the loss of telomeric sequence during passage of cells in vitro, or increase telomeric length of immortal cells in vitro. The same type of approach is also taught in PCT Publication No. 94/13383 and U.S. Pat. No. 5,484,508 which refer to methods and compositions for the determination of telomere length and telomerase activity, as well as to methods to inhibit telomerase activity in the treatment of proliferative diseases. Methods to increase or decrease the length of telomeres through an action on telomerase is also taught. The agents which are shown to reduce telomere loss of telomere length during proliferation are oligonucleotides which promote synthesis of DNA at the telomere ends, as well as telomerase.

PCT Publication No. 95/13383 discloses a method and compositions for increasing telomeric length in normal cells so as to increase the proliferative capacity of the cells and to delay the onset of cellular senescence. PCT Publication No.96/10035 teaches that telomere length serves as a biomarker for cell turnover. Furthermore, it discloses that measurement of telomere length can be used to diagnose and stage cancer and other diseases as well as cell senescence.

PCT publication WO98/11204 teaches two nucleic acid sequences termed TPC2 and TPC3 and amino acid sequences of the polypeptides encoded thereby which can be used to detect regulators of telomere length and telomerase activity in mammalian cells. TPC3 is shown to regulate telomerase activity and telomere length.

PCT publication WO98/11207 teaches telomerase reporter constructs to be used in assessing the transcriptional activity of mammalian telomerase gene transcription regulatory region. This application also relates to the use of these constructs to identify agents which modulate transcription of the telomerase gene.

Proteins that bind mammalian telomeric repeats, either to double-stranded repeats or single-stranded repeats, are also targets for telomere length regulation.

U.S. Pat. No. 5,733,730 and PCT WO97/08314 relate to the double-stranded DNA binding factor TRF and discloses a method of purifying telomerase from mammalian cells.

PCT Publication No. WO 98/00537 relates to the single-stranded DNA binding factor A1/UP1 and discloses methods and compositions to increase or decrease telomeric length. A1 is a member of the abundant family of heterogeneous nuclear ribonucleoprotein particles (hnRNP) proteins (Dreyfuss et al. 1993. Ann. Rev. Biochem. 62:289). There are over 20 such hnRNP proteins in human cells. HnRNP A1 can modulate telomere length once introduced into a mouse cell line (WO98/00537; and La Branche et al., 1998. Nat. Genet. 19:199–202). Thus, UP1 lacks the last N-terminal 124aa of A1 (the glycine-rich domain), but shares with A1 the first 196aa. The first 196aa comprises two RNA Recognition Motifs (RRMs); RRM1 extending from aa 15–93, and RRM2 extending from aa 106–184. UP1 can modulate telomere length once introduced into a mouse or a human cell line (WO98/00537; and La Branche et al., 1998., supra).

Telomeres are essential for normal cellular function, by preventing degradation and aberrant recombination of chromosome termini and facilitating the complete replication of chromosome ends. Vertebrate telomeres contain variable numbers of TAGGGT-repeats in double-stranded form and terminate with a single-stranded overhang of the G-rich strand, the strand making the 3' end of the chromosome. The ribonucleoprotein enzyme telomerase directs the synthesis of telomeric repeat units onto this G-rich strand, thereby counteracting the loss of sequence that occurs at each cell division. It is thought that the G-rich strand will then serve as substrate for the synthesis of the complementary strand by DNA primase followed by conventional DNA polymerases (Greider and Blackburn, 1989, Nature 337:331; Greider, 1996 supra).

The presence of a 3' overhang of the G-rich strand suggests that single-stranded DNA binding activities will play an important role in telomere function. Proteins that can bind to single-stranded telomeric repeats include protein α of Oxytricha, Stylonychia and Euplotes. The 56 kD protein α of Oxytricha exists as an heterodimer with the 41 kD protein β. These proteins protect single-strand overhangs from nuclease digestion and chemical modification (Fang and Cech 1995, in *Telomeres,* Blackburn, E. H., and Greider, C. W., eds, pp. 69–105, Cold Spring Harbor Press, Cold Spring Harbor, N. Y.; Gray et al., 1991, supra). Moreover, the binding of an α/α homodimer or an α/β heterodimer to telomeric DNA renders the end inaccessible to telomerase (Froelich-Ammon et al., 1998, Genes Dev 12:1504). The Chlamydomonas protein Gbp1p binds to single-stranded G-rich telomeric DNA (Johnston et al., 1999, Mol Cell Biol 19: 923), but its role in telomere function in vivo remains to be shown. While telomerase RNA makes direct contacts with single-stranded extensions during repeat synthesis, proteins components of Tetrahymena and Euplotes telomerases can also interact with telomeric single-stranded DNA substrates by protein-DNA interactions (Gandhi and Collins, 1998, Genes Dev 12:721).

In *Saccharomyces cerevisiae,* Est1p and Est4p/Cdc13p have properties of terminus-binding proteins and their association with G-rich extensions may mediate recognition by telomerase. Mutant strains engineered not to express Est1p, or expressing mutated forms of Cdc13p, undergo telomere attrition despite having wild-type levels of telomerase (Nugent et al., 1996, Science 274:249; Virta-Pearlman, et al.,1996, Genes Dev 10:3094). While Est1p interacts with telomerase RNA in vitro and in vivo, its presence is not essential in some telomerase activity assays in vitro (Steiner et al., 1996, Proc Natl Acad Sci U S A 93:2817).

In vertebrates, several proteins can interact with single-stranded G-rich extensions in vitro. However, there has been no demonstration that these proteins bind to telomeres in vivo or that their expression influences the structure of telomeres. Mammalian hnRNP proteins have been reported to associate with RNA and DNA oligonucleotides carrying telomeric repeats. The only mammalian hnRNP protein for which genetic evidence of a function in telomere biogenesis has been obtained is the hnRNP A1 protein. Ectopic expression of A1 promotes telomere elongation in mammalian cells (laBranche et al, supra). Although hnRNP A1 is a well-known modulator of alternative pre-mRNA splicing, several observations are consistent with the notion that the function of A1 is independent of its role in alternative splicing. First, a shortened derivative of A1 (UP1) that has no intrinsic activity in alternative splicing, but which can antagonize the modulatory activity of A1 in splicing extracts, also promotes telomere elongation. Second, UP1 and A1 can interact specifically with single-stranded telomeric repeats in vitro. Third, UP1 may interact with telomerase, as judged by its ability to recover telomerase activity from a cell lysate. While A1 appears to exert its effect on telomeres independently of its function in alternative splicing, it remains to be determined whether A1 has a direct role in telomere biogenesis. It also remains to be determined how the binding of A1/UP1 to telomere modulates telomere biogenesis.

There thus remains a need to modulate the length of telomeres. There also remains a need to identify agents that will enable a modulation of telomere length and/or telomere replication.

The present invention seeks to meet these and other needs.

The present description refers to a number of documents, the content of which is herein incorporated by reference in their entirety.

SUMMARY OF THE INVENTION

It is thus an aim of the present invention to provide agents and methods to modulate the length and/or replication of telomeres.

The present invention thus relates to a method to recover telomerase from a cell extract comprising a use of the interaction of UP1 with telomerase. More specifically, the invention relates to the demonstration that both A1 and UP1 interact directly and with specificity with the 5' end of human telomerase RNA (hTR).

Further, the invention relates to the binding of A1/UP1 to telomeric DNA or telomerase RNA. In addition, the invention relates to these specific interactions as valid targets to affect and modulate telomere biogenesis. In one embodiment, preventing the binding of A1 to telomeric DNA in transformed cells, or expressing A1 derivatives that may be affected in binding, can be used to compromise the integrity of telomeres and lead to cell death. In contrast, in another embodiment, improving the binding A1 would be expected to increase telomere length and forestall telomere erosion in some ageing cells.

The invention further relates to the binding of A1/UP1 to telomeric sequences which protects these sequences from nuclease attack (endonuclease and exonucleases). Thus, the present invention provides methods of interfering with A1/UP1 binding to modulate the protective capacity associated with A1/UP1 binding and affect telomere erosion. In another embodiment, the invention relates to a method for preventing A1/UP1 binding in order to produce telomeric ends that are recognized as double-stranded breaks, an event that would lead to rapid cell growth arrest.

The ability of UP1 to recover telomerase activity, and the ability of A1/UP1 to interact with human telomerase RNA suggest that another way by which A1/UP1 may control the length of telomeres is by recruiting telomerase to the ends of chromosomes. Thus, interfering with the binding of A1/UP1 to telomerase RNA would interfere with telomere maintenance and should promote telomere shortening, similar to the effects seen when the activity of telomerase is targeted.

In addition, the present invention relates to binding assays enabling a screening and an identification of agents that modulate A1/UP1 binding to telomerase RNA or telomeric DNA. Also, the present invention aims at providing bindings assays for screening for A1/UP1 derivatives that are affected in their binding abilities.

In one particular embodiment, the invention relates to a method of confirming the biological effect of agents on the binding of A1/UP1 to telomeric DNA or telomerase RNA, or of identifying agents which modulate telomere biogenesis, while not being identified as such by the binding assays of the present invention (e.g. for lack of sensitivity), comprising a testing of the effect of the agent(s) using assays that detect a biological activity which reflects the binding of A1/UP1 to a telomeric DNA or telomerase RNA. In a particular embodiment, the assay is dependent on the binding of A1/UP1 to a DNA sequence carrying multiple telomeric repeats. Non-limiting examples of such assays which detect a biological activity include: (i) an in vitro protection assay in which the binding of A1/UP1 protects against nuclease attack; (ii) an in vitro telomerase extension assay in which extension is inhibited when A1/UP1 binds to the telomeric oligonucleotide; (iii) a terminal nucleotydyl transferase (TdT) elongation assay in which 3' extension is inhibited by the binding of A1/UP1 to the substrate oligonucleotide; and (iv) a rNTP-dependent DNA polymerase assay in which the binding of A1/UP1 to the telomeric DNA substrate prevents lagging-strand synthesis. It is envisioned that such activity assays might also be used directly to screen for agents without prior testing their effects on DNA binding. Indeed, some agents may not necessarily affect A1/UP1 binding to telomeric DNA (because the assay might not be sensitive enough) but may nevertheless interfere with the activity of A1/UP1, by restoring access of the enzymes (nucleases, telomerase, TdT or polymerase) to the telomeric DNA substrate. These biological assays can also be used to test the activity of derivatives of A1/UP1, as exemplified hereinbelow for the UP1Δ1 and UP1Δ2 derivatives.

Agents, compounds or A1/UP1 derivatives identified in accordance with the present invention as affecting A1/UP1 binding and/or stimulating nuclease, telomerase, TdT or polymerase activity can then be introduced into or incubated with mammalian cells (including human transformed and/or cancer cells), and the effect on telomere structure, and/or cell growth and/or cell viability measured as described above.

While the above procedures are designed to screen for agents, compounds or A1/UP1 derivatives that reduce binding to telomeric DNA or telomerase RNA, such agents, compounds or A1/UP1 derivatives may be identified as enhancers of A1/UP1 binding. In this case, the biological assays described above will confirm their ability to improve protection against nucleases or better prevent access to telomerase, and/or TdT, and/or polymerase. Such agents can be expressed into or incubated with a variety of cells such as senescent, and/or ageing cells in culture, to test whether they improve or maintain telomere integrity during cell growth. Thus, it should be clear that the assays, methods and agents of the present invention relate broadly to modulators (which increase or decrease) of A1/UP1 binding to one of at least its target sequence.

Thus, the present invention also relates to the agents which modulate telomere biogenesis, identified by the methods and assays of the present invention.

In another embodiment of the present invention, the screening assay further comprises an administration of an agent selected as a modulator of telomere biogenesis in vitro, to an animal, tissue, cell type or tumor thereof and a determination of this administration on the animal, tissue, cell type or tumor.

In accordance with the present invention, there is therefore provided a method of identifying an agent which modulates telomere biogenesis in vitro comprising incubating a nucleic acid target sequence for A1/UP1, wherein the target nucleic acid sequence is selected from telomerase RNA and telomeric DNA, together with A1/UP1, a fragment thereof, or a derivative thereof, wherein the A1/UP1, a fragment thereof or derivative thereof is capable of binding to the target sequence; and determining at least one of a binding between said A1/UP1, or fragment, or derivative thereof and the target nucleic acid sequence and an enzymatic activity dependent on the binding between said A1/UP1, or fragment, or derivative thereof and the target nucleic acid sequence; wherein the agent is identified as a modulator of telomere biogenesis when the binding of A1/UP1, or fragment, or derivative thereof or the enzymatic activity is significantly different in the presence of the agent, as compared to in the absence thereof.

There is also provided a method of increasing lagging-strand synthesis on a telomeric sequence in vitro comprising providing of an agent which sequesters A1/UP1, a fragment thereof, or a derivative thereof.

Furthermore, there is provided a method of increasing the activity of DNA polymerase α/primase on a telomeric sequence in vitro, comprising a providing of an agent which sequesters A1/UP1.

There is further provided a method of preventing telomerase extension and/or telomere replication by DNA polymerase α/primase in vitro, comprising increasing the level of A1/UP1, or fragment thereof, or a derivative thereof available for binding to telomere.

In accordance with the present invention, there is also provided a method of maintaining the integrity of telomeric 3' overhangs comprising a providing of a A1/UP1 telomere binding domain which is capable of binding to the telomeric 3' overhangs, thereby protecting same from nuclease and/or polymerase activities.

Also in accordance with the present invention, there is also provided a method of protecting single stranded telomeric sequences against nuclease activities, comprising a providing of an A1/UP1 telomere binding domain capable of binding the single stranded telomeric sequences, thereby protecting same from the nuclease activities.

There is also provided a method of identifying an agent which modulates telomere biogenesis comprising a determination of a formation of a ternary complex made up of a telomeric sequence, A1/UP1, or fragment thereof, or fragment thereof and telomerase RNA, wherein a modulator of telomere biogenesis is identified when a level of the formation of the ternary complex is detectably different in the presence of the agent as compared to in the absence thereof.

Also provided is a method of preparing recombinant hnRNPA1 which enables a detectable binding thereto to telomerase RNA.

In accordance with the present invention, there is further provided a method of modulating telomere biogenesis comprising a disturbing of A1/UP1 telomerase RNA interaction.

In accordance with the present invention, there is also provided agents and compositions for modulating telomere biogenesis in vitro identified using an assay or method of the present invention.

In accordance with the present invention, there is also provided a method to identify an agent which modulates telomere biogenesis comprising: providing a telomerase capable of binding with A1/UP1, A1/UP1, derivative or fragment thereof and telomeric DNA, thereby creating a mixture; incubating this mixture with a candidate agent; and assessing a formation of a ternary complex comprising A1/UP1, derivative or fragment thereof, telomerase and telomeric DNA, wherein a modulator of telomere biogenesis is identified when a formulation of the ternary complex is reduced in the presence of the agent as compared to in the absence thereof.

For the purpose of the present invention, the following abbreviations and terms are defined below.

The terminology "A1/UP1" relates to hnRNPA1, its derivative UP1 having an activity in telomere biogenesis when in their native form. Non-limiting examples of this activity include binding to its target sequence (e.g. telomere DNA, telomerase RNA), protecting the telomere from nuclease digestion, and affecting lagging-strand synthesis. It will be clear to the skilled artisan (and as exemplified hereinbelow) that recombinants, derivatives or portions of A1/UP1 can also be used and tested in accordance with the present invention.

The terminology "nucleic acid target sequences for A1/UP1", or the like refer to telomere DNA and/or telomerase RNA to which A1/UP1 binds. As exemplified herein, these target sequences can be natural sequences, genetically engineered or synthetically produced. As exemplified herein, a recombinant protein comprising the N-terminal portion of hnRNPA1 up to and including RRM1 can bind specifically to telomeric DNA. Also, a recombinant protein comprising the C-terminal portion of hnRNPA1 up to and including RRM2 is sufficient for specific binding to telomerase RNA.

By "increased rate of proliferation" of a cell, it is meant that a cell has a higher rate of cell divisions compared to normal cells of that cell type, or compared to normal cells within other individuals of that cell type. Examples of such cells but not limited to these, include the $CD4^+$ cells of HIV-infected individuals, connective tissue fibroblasts associated with degenerative joint diseases, age-related muscular degeneration, astrocytes associated with Alzheimer's Disease and endothelial cells associated with atherosclerosis. In each case, one particular type of cell or a group of cells is found to be replicating at an increased level compared to surrounding cells in those tissues, or compared to normal individuals, e.g., individuals not infected with the HIV virus. Thus, the invention features administering to those cells an agent which reduces the loss of telomere length in those cells while they proliferate. The agent itself need not slow the proliferation process, but rather allow the proliferation process to continue for more cell divisions than would be observed in the absence of the agent. The agent may also be useful to slow telomere repeat loss occurring during normal aging, and for reducing telomere repeat loss while expanding cell number ex vivo for cell-based therapies. The agent could thus simply stabilize telomere length.

The assessment of the effect of agents on telomere length modulation or on telomere replication can be assessed by analyzing their effect in modulating the length of telomeres. For example, a particular cell having a known telomere length is chosen and allowed to proliferate and the length of telomere is measured during proliferation. Analysis of telomere length in cells expressing different derivatives or fragments can be identified using methods described below or other methods known to a person of ordinary skill. Non-limiting examples of such derivatives and fragments comprise hnRNP A1 in vitro mutagenized in the RRM1, RRM2 or the glycine-rich domain (see below).

Herein, hnRNP A1 and UP1 are meant to designate the nucleic acid and/or the protein. It will be recognized by a person of ordinary skill whether the protein or nucleic acid fragment is intended.

In related aspects, the present invention features a pharmaceutical composition which include therapeutically effective amounts of modulators of telomere length or replication in accordance with the present invention and pharmaceutically acceptable buffers. In one particular embodiment, these pharmaceutical compositions may include one or more of these inhibitors or agents and can be co-administered with other drugs. For example, AZT is commonly used for treatment of HIV, and may be co-administered with a telomere length reducing agent of the present invention.

In another related aspect, the invention features a method for extending the ability of a cell to replicate. In this method, a replication extending amount of an agent which is active to reduce loss of telomere length within the cell is provided during cell replication. As will be evident to those of ordinary skill in the art, this agent is similar to that useful for treatment of a condition associated with an increased rate of proliferation of a cell. However, this method is useful for the treatment of individuals not suffering from any particular condition, but in which one or more cell types are limiting in that patient, and whose life can be extended by extending the ability of those cells to continue replication. That is, the agent is added to delay the onset of cell senescence characterized by the inability of that cell to replicate further in an individual. One example of such a group of cells includes lymphocytes present in patients suffering from Downs Syndrome (although treatment of such cells may also be useful in individuals not identified as suffering from any particular condition or disease, but simply recognize that one or more cells, or collections of cells are becoming limiting in the life span of that individual).

It is notable that administration of such inhibitors or agents is not expected to be detrimental to any particular individual or animal. However, should gene therapy be used to introduce an agent of the invention into any particular cell population, care should be taken to ensure that the activity of that agent is appropriately regulated, for example, by use of a promoter which can be regulated by the nutrition of the patient. Thus, for example, the promoter may only be activated when the patient eats a particular nutrient, and is otherwise inactive. In this way, should the cell population become malignant, that individual may readily inactivate replication of the cell and cause it to become senescent simply by no longer eating that nutrient.

Another aspect of the present invention features a method for treatment of a condition associated with an elevated level of telomerase activity and/or with longer and/or more stable telomeres within a cell. The method involves administering to that cell a therapeutically effective amount of an agent that reduces or destabilizes the length of the telomeres. The level of telomerase activity can be measured in accordance with the present invention or by any other existing method or equivalent method. Example of such conditions include neoplastic (cancerous) conditions, or conditions associated with the presence of cells which are not normally present in that individual, such as protozoan parasites or opportunistic pathogens. Administration of such an agent can be achieved by any desired mean well known to those of ordinary skill in the art.

By "elevated level" of such activity, it is meant that the absolute level of telomerase activity in a particular cell is elevated compared to normal cells in that individual or compared to normal cells in other individuals not suffering from the same condition. The same principle applies to an elevated level or an elevated activity of A1 or UP1 on the length of telomeres.

In addition, the term "therapeutically effective amount" of an inhibitor is a well recognized phrase. The amount actually applied will be dependent upon the individual or animal to which treatment is to be applied, and will preferably be an optimized amount such that an inhibitory effect is achieved without significant side-effects (to the extent that those can be avoided by use of the inhibitor). That is, if effective inhibition can be achieved with no side-effects with the inhibitor at a certain concentration, that concentration should be used as opposed to a higher concentration at which side-effects may become evident. If side-effects are unavoidable, however, the minimum amount of inhibitor that is necessary to achieve the inhibition desired should be used.

By "inhibitor" is simply meant any reagent, drug or chemical which is able to inhibit the binding of A1/UP1 to telomeric DNA or telomerase RNA in vivo or in vitro, sufficiently to affect telomere biogenesis. Such inhibitors can be readily identified using standard screening protocols in which A1/UP1 and the nucleic acid is placed in contact with a potential inhibitor and the level of binding is measured in the presence or absence of the inhibitor or in the presence of varying amounts thereof. In this way, not only can useful inhibitors (or stimulators) be identified, but the optimum level of such an inhibitor (or stimulator) can be determined in vitro. Once identified as a modulator in vitro, the agent can be tested in vivo. Numerous methods to test the in vivo effect of this modulator are known to the person skilled in the art to which this application pertains.

As used herein, the terms "molecule", "compound" or "ligand" are used interchangeably and broadly to refer to natural, synthetic or semi-synthetic molecules or compounds. The term "molecule" therefore denotes for example chemicals, macromolecules, cell or tissue extracts (from plants or animals) and the like. Non limiting examples of molecules include nucleic acid molecules, peptides, antibodies, carbohydrates and pharmaceutical agents. The agents can be selected and screened by a variety of means including random screening, rational selection and by rational design using for example protein or ligand modeling methods such as computer modeling, combinatorial library screening and the like. The terms "rationally selected" or "rationally designed" are meant to define compounds which have been chosen based on the configuration of the interaction domains of the present invention. As will be understood by the person of ordinary skill, macromolecules having non-naturally occurring modifications are also within the scope of the term "molecule". For example, peptidomimetics, well known in the pharmaceutical industry and generally referred to as peptide analogs can be generated by modeling as mentioned above. Similarly, in a preferred embodiment, the polypeptides of the present invention are modified to enhance their stability. It should be understood that in most cases this modification should not alter the biological activity of the interaction domain. The molecules identified in accordance with the teachings of the present invention have a therapeutic value in diseases or conditions in which the physiology or homeostasis of the cell and/or tissue is compromised by a defect in telomere length control or modulation. Alternatively, the molecules identified in accordance with the teachings of the present invention find utility in the development of more efficient modulators of telomerase length.

As used herein, agonists and antagonists of the A1/UP1-target sequence interaction also include potentiators of known compounds with such agonist or antagonist properties. In one embodiment, agonists can be detected by contacting the indicator cell with a compound or mixture thereof or library of molecules (e.g. combinatorial library) for a fixed period time and determining a biological activity as described herein. Of course, antagonists can be similarly detected.

The therapeutic aspect of the invention is related to the now clear observation that the ability of a cell to remain immortal comprises the ability of that cell to maintain or increase the telomere length of chromosomes within that cell. Thus, therapeutic approaches for reducing the potential of a cell to remain immortal focuses on the inhibition of A1 binding, on the level thereof, on a reduction of the protective role of A1/UP1 to nucleases, on a reduction of the recruitment of telomerase by A1/UP1 and the like in those cells in which it is desirable to cause cell death. Example of such cells, but not limited to, include cancerous cells, which are one example of somatic cells which show increased length or stability of telomeres, and have become immortal. The present invention now permits such cells to become mortal once more by a reduction in the size or the stability of the telomeres. As such, inhibition can be achieved in a multitude of ways as, for example, by providing inhibitors, dominant negative mutants, derivatives of these dominant negative mutants and the like.

The inhibitors may be used for treatment of cancers of any type non-limiting examples thereof, including solid tumors and leukemias, carcinoma, histiocytic disorders, leukemia, histiocytosis malignant, Hodgkin's disease, immunoproliferative small, non-Hodgkin's lymphoma, plasmacytoma, reticuloendotheliosis, melanoma and the like, osteosarcoma, rhabdomyosarcoma, sarcoma, neoplasms, and for any treatment or of all other conditions in which cells have become immortalized.

In other cases, it is important to slow the loss of telomere sequences, in particular, cells in association with certain diseases (although such treatment is not limited to this, it can be used in normal ageing and ex vivo treatments). For example, some diseases display abnormal fast rate of proliferation of one or more particular groups of cells. One example of such a disease is AIDS, in which death is caused by the early senescence of $CD4^+$cells. It is important to note that such cells age, not because of abnormal loss of telomere sequences (although this may be a factor) but rather because the replicative rate of the $CD4^+$cells is increased such that telomere attrition occurs at a greater rate than normal for that group of cells (Lundblad and Wright, 1996, Cell 87:369). Thus, the present invention provides means to stabilize the length of telomeres. The applicant therefore is providing therapeutic agents which can be used in the treatment of such diseases, and in addition, the means of diagnostic procedures by which similar diseases can be detected so that appropriate therapeutic protocols can be devised and implemented.

Specifically, the loss of telomeres within any particular cell population can be reduced by providing thereto telomere length stabilizing agents, telomere replication stimulators and the like, enhancers of telomerase recruitment to the telomere, "nuclease inhibitors", according to the present invention. These molecules can be provided within a cell in order to reduce telomere loss or to make that cell immortal. Those of ordinary skill in the art will recognize that other enzymatic activities may be used to enhance the lengthening of telomeres within such cells, for example, by providing certain viral sequences within a cell, non-limiting examples thereof include EBV and SV40. In addition, equivalent such molecules, or other molecules may be readily screened to determine those that will reduce loss of telomeres or stabilize the length of same. Such screening may occur in vitro, and the therapeutic agents discovered by such screening utilized in the above method in vivo. It should be understood that in some situations, in vitro assays such as gel shifts might be sufficient to assess the telomere length stabilizing activity of an agent. In other cases, the assessment of telomere length per se (as opposed to binding of an agent to the telomere) might have to be ascertained in cultured cells for example. The skilled artisan will be able to determine which assay (which are not limited to two listed above) is sufficient to determine the effect of the tested agent on telomere length. As described below, the present invention also provides methods and assays to screen for agents which modulate telomere biogenesis, by assessing an enzymatic activity which is affected by the binding of A1/UP1 to one target sequence thereof (e.g. telomere DNA, telomerase RNA).

Nucleotide sequences are presented herein by single strand, in the 5' to 3' direction, from left to right, using the one letter nucleotide symbols as commonly used in the art and in accordance with the recommendations of the IUPAC-IUB Biochemical Nomenclature Commission.

Unless defined otherwise, the scientific and technological terms and nomenclature used herein have the same meaning as commonly understood by a person of ordinary skill to which this invention pertains. Generally, the procedures for cell cultures, infection, molecular biology methods and the like are common methods used in the art. Such standard techniques can be found in reference manuals such as for example Sambrook et al. (1989, Molecular Cloning—A Laboratory Manual, Cold Spring Harbor Laboratories) and Ausubel et al. (1994, Current Protocols in Molecular Biology, Wiley, New York).

The present description refers to a number of routinely used recombinant DNA (rDNA) technology terms. Nevertheless, definitions of selected examples of such rDNA terms are provided for clarity and consistency.

As used herein, "nucleic acid molecule", refers to a polymer of nucleotides. Non-limiting examples thereof include DNA (i.e. genomic DNA, cDNA) and RNA molecules (i.e. mRNA). The nucleic acid molecule can be obtained by cloning techniques or synthesized. DNA can be double-stranded or single-stranded (coding strand or non-coding strand [antisense]).

The term "recombinant DNA" as known in the art refers to a DNA molecule resulting from the joining of DNA segments. This is often referred to as genetic engineering.

The term "DNA segment", is used herein, to refer to a DNA molecule comprising a linear stretch or sequence of nucleotides. This sequence when read in accordance with the genetic code, can encode a linear stretch or sequence of amino acids which can be referred to as a polypeptide, protein, protein fragment and the like.

The terminology "amplification pair" refers herein to a pair of oligonucleotides (oligos) of the present invention, which are selected to be used together in amplifying a selected nucleic acid sequence by one of a number of types of amplification processes, preferably a polymerase chain reaction. Other types of amplification processes include ligase chain reaction, strand displacement amplification, or nucleic acid sequence-based amplification, as explained in greater detail below. As commonly known in the art, the oligos are designed to bind to a complementary sequence under selected conditions.

The nucleic acid (i.e. DNA or RNA) for practicing the present invention may be obtained according to well known methods.

Oligonucleotide probes or primers of the present invention may be of any suitable length, depending on the particular assay format and the particular needs and targeted genomes employed. In general, the oligonucleotide probes or primers are at least 12 nucleotides in length, preferably between 15 and 24 molecules, and they may be adapted to be especially suited to a chosen nucleic acid amplification system. As commonly known in the art, the oligonucleotide probes and primers can be designed by taking into consideration the melting point of hybridization thereof with its targeted sequence (see below and in Sambrook et al., 1989, Molecular Cloning—A Laboratory Manual, 2nd Edition, CSH Laboratories; Ausubel et al., 1989, in Current Protocols in Molecular Biology, John Wiley & Sons Inc., N.Y.).

The term "oligonucleotide" or "DNA" molecule or sequence refers to a molecule comprised of the deoxyribonucleotides adenine (A), guanine (G), thymine (T) and/or cytosine (C), in a double-stranded form, and comprises or includes a "regulatory element" according to the present invention, as the term is defined herein. The term "oligonucleotide" or "DNA" can be found in linear DNA molecules or fragments, viruses, plasmids, vectors, chromosomes or synthetically derived DNA. As used herein, particular double-stranded DNA sequences may be described according to the normal convention of giving only the sequence in the 5' to 3' direction. "Nucleic acid hybridization" refers generally to the hybridization of two single-stranded nucleic acid molecules having complementary base sequences, which under appropriate conditions will form a thermodynamically favored double-stranded structure. Examples of hybridization conditions can be found in the two laboratory manuals referred above (Sambrook et al., 1989, supra and Ausubel et al., 1989, supra) and are commonly known in the art. In the case of a hybridization to a nitrocellulose filter, as for example in the well known Southern blotting procedure, a nitrocellulose filter can be incubated overnight at 65° C. with a labeled probe in a solution containing 50% formamide, high salt (5×SSC or 5×SSPE), 5×Denhardt's solution, 1% SDS, and 100 μg/ml denatured carrier DNA (i.e. salmon sperm DNA). The non-specifically binding probe can then be washed off the filter by several washes in 0.2×SSC/0.1% SDS at a temperature which is selected in view of the desired stringency: room temperature (low stringency), 42° C. (moderate stringency) or 65° C. (high stringency). The selected temperature is based on the melting temperature (Tm) of the DNA hybrid. Of course, RNA-DNA hybrids can also be formed and detected. In such cases, the conditions of hybridization and washing can be adapted according to well known methods by the person of ordinary skill. Stringent conditions will be preferably used (Sambrook et al., 1989, supra).

Probes of the invention can be utilized with naturally occurring sugar-phosphate backbones as well as modified backbones including phosphorothioates, dithionates, alkyl phosphonates and α-nucleotides and the like. Modified sugar-phosphate backbones are generally taught by Miller, 1988, Ann. Reports Med. Chem. 23:295 and Moran et al., 1987, Nucleic Acids Res., 14:5019. Probes of the invention can be constructed of either ribonucleic acid (RNA) or deoxyribonucleic acid (DNA).

The types of detection methods in which probes can be used include Southern blots (DNA detection), dot or slot blots (DNA, RNA), and Northern blots (RNA detection). Although less preferred, labeled proteins could also be used to detect a particular nucleic acid sequence to which it binds. Other detection methods include kits containing probes on a dipstick setup and the like.

Although the present invention is not specifically dependent on the use of a label for the detection of a particular nucleic acid sequence, such a label might be beneficial, by increasing the sensitivity of the detection. Furthermore, it enables automation. Probes can be labeled according to numerous well known methods (Sambrook et al., 1989, supra). Non-limiting examples of labels include $^{3}H$, $^{14}C$, $^{32}P$, and $^{35}S$. Non-limiting examples of detectable markers include ligands, fluorophores, chemiluminescent agents, enzymes, and antibodies. Other detectable markers for use with probes, which can enable an increase in sensitivity of the method of the invention, include biotin and radionucleotides. It will become evident to the person of ordinary skill that the choice of a particular label dictates the manner in which it is bound to the probe.

As commonly known, radioactive nucleotides can be incorporated into probes of the invention by several methods. Non-limiting examples thereof include kinasing the 5' ends of the probes using gamma $^{32}P$ ATP and polynucleotide kinase, using the Klenow fragment of Pol I of E. coli in the presence of radioactive dNTP (i.e. uniformly labeled DNA probe using random oligonucleotide primers in low-melt gels), using the SP6/T7 system to transcribe a DNA segment in the presence of one or more radioactive NTP, and the like.

As used herein, "oligonucleotides" or "oligos" define a molecule having two or more nucleotides (ribo or deoxyribonucleotides). The size of the oligo will be dictated by the particular situation and ultimately on the particular use thereof and adapted accordingly by the person of ordinary skill. An oligonucleotide can be synthetised chemically or derived by cloning according to well known methods.

As used herein, a "primer" defines an oligonucleotide which is capable of annealing to a target sequence, thereby creating a double stranded region which can serve as an initiation point for DNA synthesis under suitable conditions.

Amplification of a selected, or target, nucleic acid sequence may be carried out by a number of suitable methods. See generally Kwoh et al., 1990, Am. Biotechnol. Lab. 8:14–25. Numerous amplification techniques have been described and can be readily adapted to suit particular needs of a person of ordinary skill. Non-limiting examples of amplification techniques include polymerase chain reaction (PCR), ligase chain reaction (LCR), strand displacement amplification (SDA), transcription-based amplification, the Qβ replicase system and NASBA (Kwoh et al., 1989, Proc. Natl. Acad. Sci. USA 86,1173–1177; Lizardi et al., 1988, Bio Technology 6:1197–1202; Malek et al., 1994, Methods Mol. Biol., 28:253–260; and Sambrook et al., 1989, supra). Preferably, amplification will be carried out using PCR.

Polymerase chain reaction (PCR) is carried out in accordance with known techniques. See, e.g., U.S. Pat. Nos. 4,683,195; 4,683,202; 4,800,159; and 4,965,188 (the disclosures of all three U.S. Patent are incorporated herein by reference). In general, PCR involves, a treatment of a nucleic acid sample (e.g., in the presence of a heat stable DNA polymerase) under hybridizing conditions, with one oligonucleotide primer for each strand of the specific sequence to be detected. An extension product of each primer which is synthesized is complementary to each of the two nucleic acid strands, with the primers sufficiently complementary to each strand of the specific sequence to hybridize therewith. The extension product synthesized from each primer can also serve as a template for further synthesis of extension products using the same primers. Following a sufficient number of rounds of synthesis of extension products, the sample is analyzed to assess whether the sequence or sequences to be detected are present. Detection of the amplified sequence may be carried out by visualization following EtBr staining of the DNA following gel electrophores, or using a detectable label in accordance with known techniques, and the like. For a review on PCR techniques (see PCR Protocols, A Guide to Methods and Amplifications, Michael et al. Eds, Acad. Press, 1990).

Ligase chain reaction (LCR) is carried out in accordance with known techniques (Weiss, 1991, Science 254:1292). Adaptation of the protocol to meet the desired needs can be carried out by a person of ordinary skill. Strand displacement amplification (SDA) is also carried out in accordance with known techniques or adaptations thereof to meet the particular needs (Walker et al., 1992, Proc. Natl. Acad. Sci. USA 89:392–396; and ibid., 1992, Nucleic Acids Res. 20:1691–1696).

As used herein, the term "gene" is well known in the art and relates to a nucleic acid sequence defining a single protein or polypeptide. A "structural gene" defines a DNA sequence which is transcribed into RNA and translated into a protein having a specific amino acid sequence thereby giving rise the a specific polypeptide or protein. It will be readily recognized by the person of ordinary skill, that the nucleic acid sequence of the present invention can be incorporated into anyone of numerous established kit formats which are well known in the art.

A "heterologous" (i.e. a heterologous gene) region of a DNA molecule is a subsegment segment of DNA within a larger segment that is not found in association therewith in nature. The term "heterologous" can be similarly used to define two polypeptidic segments not joined together in nature. Non-limiting examples of heterologous genes include reporter genes such as luciferase, chloramphenicol acetyl transferase, β-galactosidase, and the like which can be juxtaposed or joined to heterologous control regions or to heterologous polypeptides.

The term "vector" is commonly known in the art and defines a plasmid DNA, phage DNA, viral DNA and the like, which can serve as a DNA vehicle into which DNA of the present invention can be cloned. Numerous types of vectors exist and are well known in the art.

The term "expression" defines the process by which a gene is transcribed into mRNA (transcription), the mRNA is then being translated (translation) into one polypeptide (or protein) or more.

The terminology "expression vector" defines a vector or vehicle as described above but designed to enable the expression of an inserted sequence following transformation into a host. The cloned gene (inserted sequence) is usually placed under the control of control element sequences such as promoter sequences. The placing of a cloned gene under such control sequences is often referred to as being operably linked to control elements or sequences.

Operably linked sequences may also include two segments that are transcribed onto the same RNA transcript. Thus, two sequences, such as a promoter and a "reporter sequence" are operably linked if transcription commencing in the promoter will produce an RNA transcript of the reporter sequence. In order to be "operably linked" it is not necessary that two sequences be immediately adjacent to one another.

Expression control sequences will vary depending on whether the vector is designed to express the operably linked gene in a prokaryotic or eukaryotic host or both (shuttle vectors) and can additionally contain transcriptional elements such as enhancer elements, termination sequences, tissue-specificity elements, and/or translational initiation and termination sites.

Prokaryotic expressions are useful for the preparation of large quantities of the protein encoded by the DNA sequence of interest. This protein can be purified according to standard protocols that take advantage of the intrinsic properties thereof, such as size and charge (i.e. SDS gel electrophoresis, gel filtration, centrifugation, ion exchange chromatography . . . ). In addition, the protein of interest can be purified via affinity chromatography using polyclonal or monoclonal antibodies. The purified protein can be used for therapeutic applications.

The DNA construct can be a vector comprising a promoter that is operably linked to an oligonucleotide sequence of the present invention, which is in turn, operably linked to a heterologous gene, such as the gene for the luciferase reporter molecule. "Promoter" refers to a DNA regulatory region capable of binding directly or indirectly to RNA polymerase in a cell and initiating transcription of a downstream (3' direction) coding sequence. For purposes of the present invention, the promoter is bound at its 3' terminus by the transcription initiation site and extends upstream (5' direction) to include the minimum number of bases or elements necessary to initiate transcription at levels detectable above background. Within the promoter will be found a transcription initiation site (conveniently defined by mapping with S1 nuclease), as well as protein binding domains (consensus sequences) responsible for the binding of RNA polymerase. Eukaryotic promoters will often, but not always, contain "TATA" boses and "CCAT" boxes. Prokaryotic promoters contain −10 and −35 consensus sequences which serve to initiate transcription and the transcript products contain Shine-Dalgarno sequences which serve as ribosome binding sequences during translation initiation.

As used herein, the designation "functional derivative" denotes, in the context of a functional derivative of a sequence whether an nucleic acid or amino acid sequence, a molecule that retains a biological activity (either functional or structural) that is substantially similar to that of the original sequence. This functional derivative or equivalent may be a natural derivatives or may be prepared synthetically. Such derivatives include amino acid sequences having substitutions, deletions, or additions of one or more amino acids, provided that the biological activity of the protein is conserved. The same applies to derivatives of nucleic acid sequences which can have substitutions, deletions, or additions of one or more nucleotides, provided that the biological activity of the sequence is generally maintained. When relating to a protein sequence, the substituting amino acid as chemico-physical properties which are similar to that of the substituted amino acid. The similar chemico-physical properties include, similarities in charge, bulkiness, hydrophobicity, hydrophylicity and the like. The term "functional derivatives" is intended to include "fragments", "segments", "variants", "analogs" or "chemical derivatives" of the subject matter of the present invention.

Thus, the term "variant" refers herein to a protein or nucleic acid molecule which is substantially similar in structure and biological activity to the protein or nucleic acid of the present invention.

The functional derivatives of the present invention can be synthesized chemically or produced through recombinant DNA technology, all these methods are well known in the art.

As used herein, "chemical derivatives" is meant to cover additional chemical moieties not normally part of the subject matter of the invention. Such moieties could affect the physico-chemical characteristic of the derivative (i.e. solubility, absorption, half life and the like, decrease of toxicity). Such moieties are exemplified in Remington's Pharmaceutical Sciences (1980). Methods of coupling these chemical-physical moieties to a polypeptide are well known in the art.

The term "allele" defines an alternative form of a gene which occupies a given locus on a chromosome.

As commonly known, a "mutation" is a detectable change in the genetic material which can be transmitted to a daughter cell. As well known, a mutation can be, for example, a detectable change in one or more deoxyribonucleotide. For example, nucleotides can be added, deleted, substituted for, inverted, or transposed to a new position. Spontaneous mutations and experimentally induced mutations exist. The result of a mutations of nucleic acid molecule is a mutant nucleic acid molecule. A mutant polypeptide can be encoded from this mutant nucleic acid molecule.

As used herein, the term "purified" refers to a molecule having been separated from a cellular component. Thus, for example, a "purified protein" has been purified to a level not found in nature. A "substantially pure" molecule is a molecule that is lacking in all other cellular components.

In certain embodiments, it might be beneficial to use fusion proteins comprising the protein of the present invention, a part thereof or a derivative thereof. Non limiting examples of such fusion proteins include a hemaglutinin fusions and Gluthione-S-transferase (GST) fusions and Maltose binding protein (MBP) fusions. In certain embodiments, it might be beneficial to introduce a protease cleavage site between the two polypeptide sequences which have been fused. Such protease cleavage sites between two heterologously fused polypeptides are well known in the art.

In certain embodiments, it might also be beneficial to fuse the protein of the present invention, a part thereof or a derivative thereof, to signal peptide sequences enabling a secretion of the fusion protein from the host cell. Signal peptides from diverse organisms are well known in the art. Bacterial OmpA and yeast Suc2 are two non-limiting examples of proteins containing signal sequences. In certain embodiments, it might also be beneficial to introduce a linker (commonly known) between the interaction domain and the heterologous polypeptide portion. Such fusion protein find utility in the assays of the present invention as well as for purification purposes, detection purposes and the like.

For certainty, the sequences and polypeptides useful to practice the invention include without being limited thereto mutants, homologs, subtypes, alleles and the like. It shall be understood that generally, the sequences of the present invention should encode a functional (albeit defective) interaction domain. It will be clear to the person of ordinary skill that whether an interaction domain of the present invention, variant, derivative, or fragment thereof retains its function in binding to its partner can be readily determined by using the teachings and assays of the present invention and the general teachings of the art.

As exemplified herein below, the protein of the present invention, a part thereof or a derivative thereof, can be modified, for example by in vitro mutagenesis, to dissect the structure-function relationship thereof and permit a better design and identification of modulating compounds. However, some derivative or analogs having lost their biological function may still find utility, for example for raising antibodies. These antibodies could be used for detection or purification purposes. In addition, these antibodies could also act as competitive or non-competitive inhibitors and be found to be modulators of protease activity.

The antibodies of the present invention include monoclonal and polyclonal antibodies, as well as fragments of these antibodies. The invention further includes single chain antibodies. Antibody fragments which contain the idiotype of the molecule can be generated by known techniques. For example, such fragments include but are not limited to: the $F(ab')_2$ fragment; the Fab' fragments, Fab fragments, and Fv fragments.

Of special interest to the present invention are produced in humans, or are "humanized" (i.e. non-immunogenic in a human) by recombinant or other technology. Humanized antibodies can be produced for example by replacing an immunogenic portion of an antibody with a corresponding, but non-immunogenic portion (i.e. chimeric antibodies) (Robinson et al., International Patent Publication PCT/US86/02269; Akira et al., European Patent Application 184,187; Taniguchi, European Patent Application 171,496. Reviews on humanized chimeric antibodies include Morrison, 1985, Science 229: 1202–1207 and Oi et al., 1986, BioTechniques 4:214.

In general, techniques for preparing monoclonal antibodies and hybridomas are well known in the art (Campbell, 1984, supra; Harlow et al., 1988, supra; and St. Groth et al., 1980, J. Immunol. Methods 35: 1–21. In general, techniques for purifying monoclonal antibodies are also well known in the art (Campbell, 1984, supra; Harlow et al., 1988, supra). Non-limiting examples of monoclonal antibody purification methods include ammonium sulfate precipitation, ion exchange chromatography and HPLC. Monoclonal antibodies can also be produced by bioreactor such as the hollow fiber cell culture system described in (the Unisyn instruction manuel). For example, using this hollow fiber membrane having a molecular weight cut off of 35.000, $1 \times 10^8$ cells of hybridoma are introduced into the bioreactor. The hybridoma can be grown in PFHM-11 media (GIBCO, BRL) with PEN/STREP (GIBCO/BRL). In certain embodiments of the present invention, it might be advantageous to provide the above-described antibodies as detectably labeled.

From the specification and appended claims, the term therapeutic agent should be taken in a broad sense so as to also include a combination of at least two such therapeutic agents. Further, the DNA segments or proteins according to the present invention can be introduced into individuals in a number of ways. For example, erythropoietic cells can be isolated from the afflicted individual, transformed with a DNA construct according to the invention and reintroduced to the afflicted individual in a number of ways, including intravenous injection. Alternatively, the DNA construct can be administered directly to the afflicted individual, for example, by injection in the bone marrow. The DNA construct can also be delivered through a vehicle such as a liposome, which can be designed to be targeted to a specific cell type, and engineered to be administered through different routes.

For administration to humans, the prescribing medical professional will ultimately determine the appropriate form and dosage for a given patient, and this can be expected to vary according to the chosen therapeutic regimen (i.e. DNA construct, protein, cells), the response and condition of the patient as well as the severity of the disease.

Composition within the scope of the present invention should contain the active agent (i.e. fusion protein, nucleic acid, and molecule) in an amount effective to achieve the desired therapeutic effect while avoiding adverse side effects. Typically, the nucleic acids in accordance with the present invention can be administered to mammals (i.e. humans) in doses ranging from 0.005 to 1 mg per kg of body weight per day of the mammal which is treated. Pharmaceutically acceptable preparations and salts of the active agent are within the scope of the present invention and are well known in the art (Remington's Pharmaceutical Science, 16th Ed., Mack Ed.). For the administration of polypeptides, antagonists, agonists and the like, the amount administered should be chosen so as to avoid adverse side effects. The dosage will be adapted by the clinician in accordance with conventional factors such as the extent of the disease and different parameters from the patient. Typically, 0.001 to 50 mg/kg/day will be administered to the mammal.

Other objects features and advantages of the present invention will become apparent upon reading of the following non-restrictive description of the preferred embodiments thereof given by way of example only with reference to the accompanying drawings and from the claims.

BRIEF DESCRIPTION OF THE DRAWINGS

Having thus generally described the invention, reference will now be made to the accompanying drawings, showing by way of illustration a preferred embodiment thereof, and in which:

FIG. 5 shows that A1/UP1 inhibits extension by telomerase in vitro. A, A1 and UP1 inhibit telomerase activity. Telomerase extension assays were performed in a HeLa S100 extract using TS10 as substrate (0.5 $\mu$M). UP1, G-A1 and gp32 at concentrations of 1.25, 2.5 and 8 $\mu$M were added to TS10 before incubation in the S100 mixture. B, gel-shift assay with UP1 and gp32. UP1 and gp32 at concentrations of 0.45, 0.9 and 1.8 $\mu$M were incubated with TS10 (0.5 $\mu$M). Complexes were fractionated on 5% non-denaturating polyacrylamide gels. The position of complexes and free TS10 is shown. C, UP1 inhibits the extension of shorter substrates. TS or TS1 (0.5 $\mu$M) was added to UP1 (8 $\mu$M) before incubation in the S100 mixture. The length of the extension products is indicated on the left. The sequence at the 3' end of each oligo is shown below in upper case, and the nucleotides added by telomerase are in lower case. D, an excess of oligonucleotide bound by UP1 can rescue telomere extension on TS10. TS8A or the control oligonucleotide MS2 (1 or 2 $\mu$M) were incubated with UP1 (3 $\mu$M) before addition to a mixture containing the S100 extract, TS10 (0.5 $\mu$M) and dNTPs. E, a UP1 derivative lacking the second RRM (G-UP1Δ2) does not prevent telomerase extension. UP1 and G-UP1Δ2 proteins were used at concentrations of 2.25 $\mu$M and 7 $\mu$M in the assay.

FIG. 6 shows that UP1 represses TdT activity. UP1, GST-UP1Δ2, GST-UP1Δ1 and gp32 were prebound to TS10 (20 nM) followed by the addition of TdT. The concentrations of proteins used are indicated in $\mu$M above each lane.

FIG. 10 shows that A1 binds to hTR. The binding of different preparations of recombinant A1 is shown. (A) Procedure I was used in LaBranche et al. (1998) to prepare rA1 that, in contrast to UP1, was unable to recover telomerase activity from a cell extract. In comparison to rUP1 made using the same procedure, this preparation of rA1 binds weakly to hTR-A (lanes 2–4). (B) When procedure II is used, rA1 binds to hTR-A (lanes 9–14) at least as efficiently as rUP1 (lanes 2–7).

FIG. 11 shows that the binding to hTR requires RRM2. (A) Structure of the UP1 derivatives. (B) Gel-shift assays with UP1Δ1 and UP1Δ2. Binding was performed using hTR-A (lanes 1–3) or hTR-B (lanes 3–6). (C) A telomeric oligo does not efficiently compete UP1 binding to a telomerase RNA transcript. UP1 (5 pmoles) and the $^{32}$P-labeled RNA were incubated in the presence of increasing amounts of the telomeric oligo TS10.

FIG. 13 shows that the TS10/rA1/hTR-A ternary complex resists incubation in a nuclear extract. Left panel: hTR-A and rA1 were mixed and loaded onto the TS10 column essentially as described in the legend of FIG. 4B. Middle panel: hTR-A and rA1 were incubated together and mix in a HeLa S100 extract. The mixture was then loaded onto a TS10 column. Right panel: same as in middle panel except that rA1 was omitted. I=Input (total fraction), FT=flow-through fraction (total fraction), We (wash fraction). Elution 1, 2, 3 and 4 are successive elutions with buffer DN containing 250 mM, 500 mM, 750 mM and 1M NaCl, respectively. The position of hTR-A is indicated.

Other objects, advantages and features of the present invention will become more apparent upon reading of the following non-restrictive description of preferred embodiments with reference to the accompanying drawing which is exemplary and should not be interpreted as limiting the scope of the present invention.

DESCRIPTION OF THE PREFERRED EMBODIMENT

The hnRNP A1 protein and a shortened derivative (UP1) promote telomere elongation in mammalian cells. To gain insights into the function of A1/UP1 in telomere biogenesis, the binding properties of recombinant A1/UP1 and derivatives to single-stranded DNA oligonucleotides were investigated. The results presented herein below indicate that UP1 preferably binds to DNA carrying single-stranded telomeric extensions at the 3' terminus. The RNA-recognition motif 1 (RRM1) is sufficient for strong and specific binding to oligomers carrying vertebrate telomeric repeats. It is also shown that the binding of A1/UP1 protects telomeric sequences against degradation by endo- and exonucleases. Moreover, A1/UP1 binding prevents extension by telomerase and terminal deoxynucleotidytransferase, and inhibits rNTP-dependent DNA synthesis in vitro. Taken together, these observations show that A1/UP1 is a telomere end-binding protein, which plays key roles in the maintenance of long 3' overhangs. Thus, the results presented here show that A1/UP1 can contribute to telomere protection and can modulate telomere replication in vitro.

A1 and UP1 Binding to Telomeric Repeats

Figure 1:
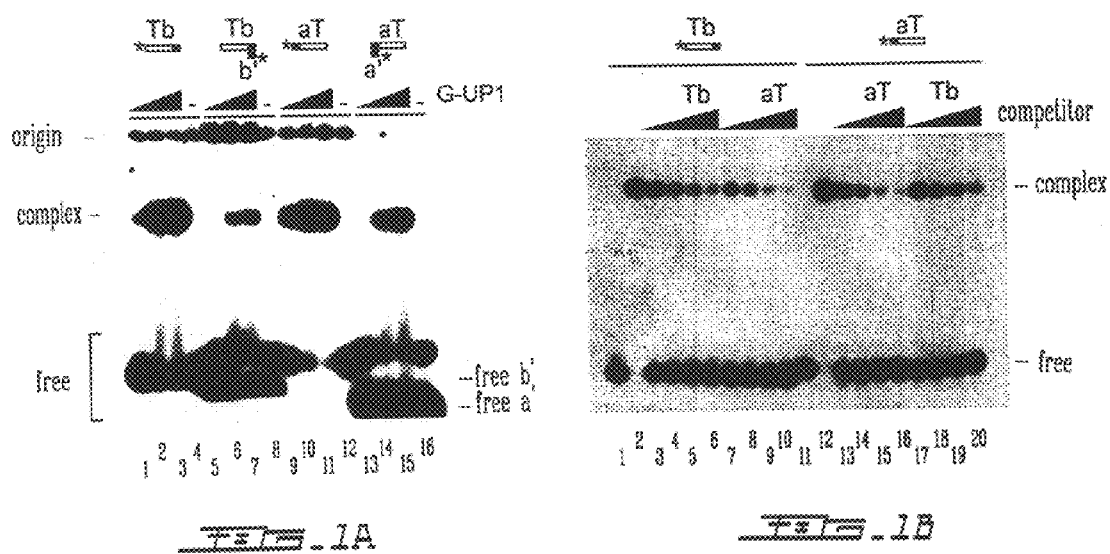
FIG. 1 shows the binding of UP1 to single-stranded telomeric extensions. Gel-shift assays were performed using single-stranded or partially double-stranded duplex substrates. A, the concentrations of GST-UP1 (G-UP1) used for each set of DNA substrate were 0.25, 0.5, 1.0 and 0 $\mu$M. Duplex formation was accomplished by incubating an equimolar amount of unlabeled Tb with labeled b' (or unlabeled aT with labeled a'). The partial duplex substrates migrate slightly above the position of labeled Tb and aT. G-UP1 did not bind to a' and b' alone (not shown). B, gel shift assays were accomplished in the presence of an excess of cold oligonucleotides as competitor. Labeled Tb or aT (0.1 $\mu$M) was used in combination with cold Tb or aT (0, 0.625, 1.25, 2.5 and 5.0 $\mu$M) and G-UP1 (0.3 $\mu$M). (Open bar) vertebrate telomeric repeats; (solid bar) nontelomeric DNA. The asterisk (*) indicates which oligonucleotide was $^{32}$P-labeled at its 5' end. Complexes were fractionated on 5% non-denaturating polyacrylamide gels. The position of the free and complexed oligonucleotides is shown.

It has been reported that recombinant forms of the A1 and UP1 proteins (GST-A1 and GST-UP1) can bind directly and specifically to short single-stranded oligonucleotides carrying two to four contiguous vertebrate TAGGGT telomeric repeats. As monitored by gel-shift assays, A1 and UP1 did not bind to a 22 nt yeast telomeric sequence (data not shown). Because mammalian chromosomes end with G-rich single-stranded overhangs, the influence of non-telomeric sequences flanking the telomeric repeats was tested. Binding assays using UP1 and oligonucleotides carrying non-telomeric sequences upstream or downstream of the telomeric cassette indicated a slight preference for telomeric repeats located at the 3' end (FIG. 1A, compare lanes 1–3 with lanes 9–11). Likewise, UP1 bound slightly more efficiently to oligonucleotides carrying a double-stranded portion at the 5' end rather than at the 3' end (FIG. 1A, compare lanes 5–7 with lanes 13–15). Binding assays performed in the presence of an excess of unlabeled competitor oligomers confirmed that UP1 interacts slightly better with an oligomer that contains telomeric sequences at the 3' terminus (FIG. 1B).

Figure 2:
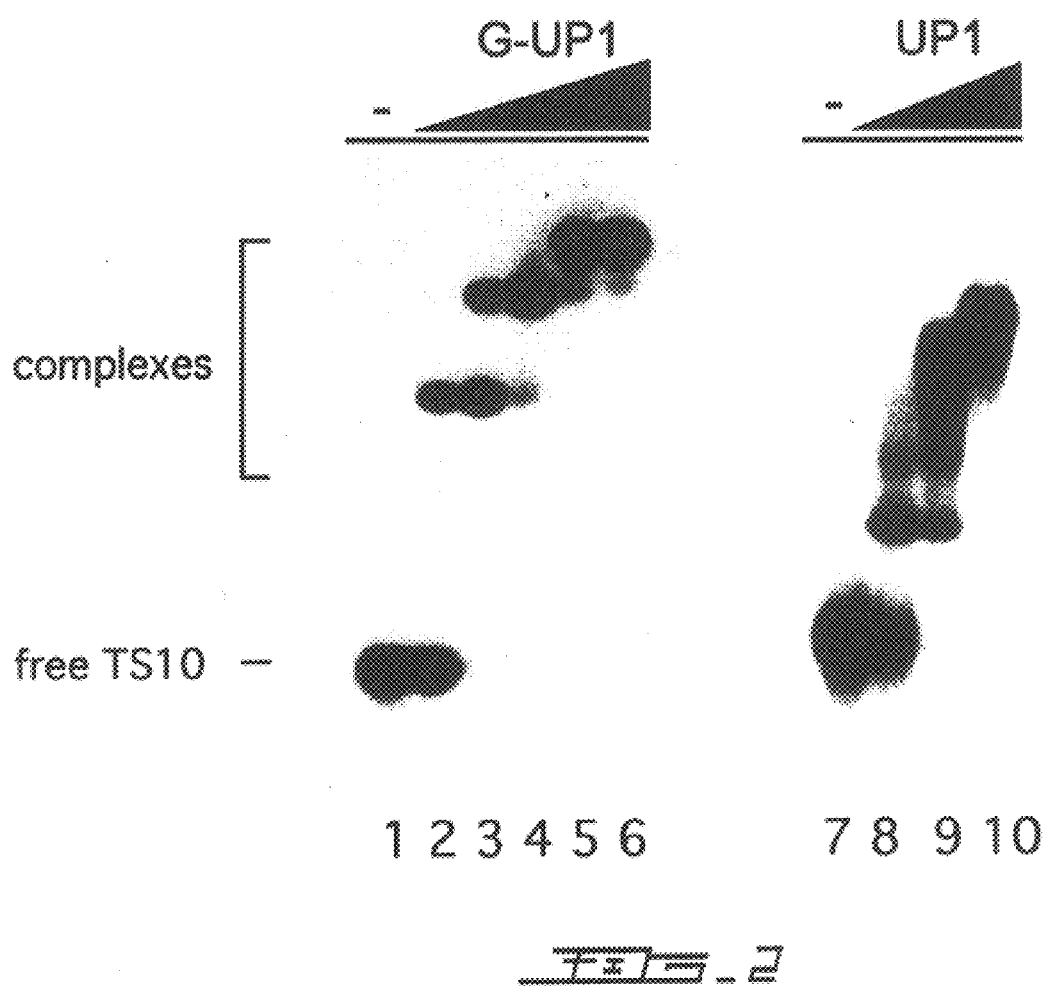
FIG. 2 shows the binding of UP1 to a long telomeric extension. GST-UP1 (G-UP1) at concentrations of 0, 0.2, 0.5, 1.0, 2.0 and 4.0 $\mu$M, or UP1 at concentrations of 0, 1.0, 2.0 and 4.0 $\mu$M, were incubated with TS10 (0.5 $\mu$M). Complexes were fractionated on 5% non-denaturating polyacrylamide gels. The position of complexes and free TS10 is shown.

Because the length of single-stranded G-rich overhangs in human and mouse telomeres ranges from 50 to 150 nucleotides, the binding of A1/UP1 to a more natural substrate (TS10) containing 10 contiguous telomeric TTAGGG repeats and, hence, 9 complete A1 binding sites (TAGGGT) was examined. A mobility shift assay performed with GST-UP1 revealed the assembly of three complexes with TS10 (FIG. 2, lanes 1–6). A similar result was obtained with GST-A1, and no complex was formed when GST-A1 or GST-UP1 was incubated with a control oligonucleotide of similar length (data not shown). The profile of complex formation on TS10 was different when a preparation of UP1 lacking the GST moiety was used (FIG. 2, lanes 8–10). In this case, a small complex appeared at low concentration of UP1, several complexes of intermediate mobility appeared as the concentration of UP1 was increased, and a single highly retarded complex was detected at the highest concentration of UP1. Thus, although the presence of a bulky GST domain does not dramatically affect the affinity of UP1 to TS10, it influences the architecture of the complex.

RRM1 Is Sufficient for Strong and Specific Binding to Telomeric Sequences

Figure 3A:
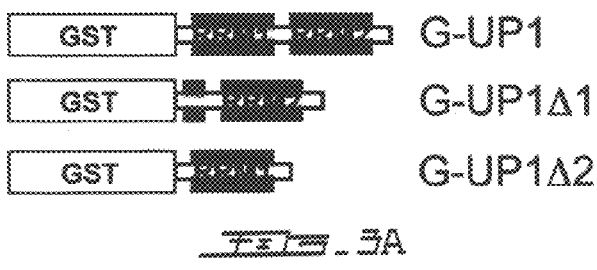
FIG. 3 shows the binding of UP1 and UP1 derivatives lacking RRM1 or RRM2. A, structure of the recombinant GST-UP1, GST-UP1Δ1 and GST-UP1Δ2 proteins. B, proteins were purified on glutathione-Sepharose, fractionated on SDS-PAGE and stained with Coomassie blue. M=molecular weight markers. C, TS10 (0.3 nM) was incubated with the indicated concentrations (in $\mu$M) of G-UP1, G-UP1Δ1 and G-UP1Δ2. Binding was measured by a gel-shift assay and is expressed as a percentage of the input labeled material that formed complexes. D, binding of UP1Δ2 (1 $\mu$M) to different small oligomers (0.02 $\mu$M). The identity of the oligonucleotides is shown above each lane.
Figure 3B:
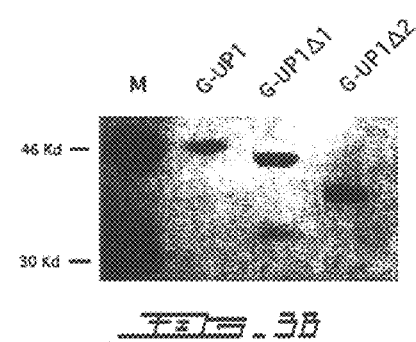

To determine whether the binding of UP1 to telomeric sequences requires both nucleic acid binding domains, the binding activity of UP1 molecules deprived of either RRM2 or part of RRM1 was tested (FIG. 3A and 3B). The UP1 derivative lacking the C-terminal RRM2 domain (UP1Δ2) was almost as efficient as the complete UP1 protein at binding to TS10 (FIG. 3C). The binding of UP1Δ2 remained specific, as short oligonucleotides carrying mutated telomeric repeats were less efficiently bound by UP1Δ2 (FIG. 3D). A UP1 derivative lacking most of RRM1 (UP1Δ1) was considerably less efficient than UP1 and UP1Δ2 at binding to TS10 (FIG. 3C). These results indicate that the N-terminal portion of UP1 that contains RRM1 is sufficient for stable and specific binding. As stable UP1 binding requires a minimum of two TAGGGT units, each unit may be bound by the RRM1 domain of one UP1 molecule.

A1 and UP1 Can Protect Telomeric Sequences from Nuclease Digestion

Figures 4A, 4B, 4C:
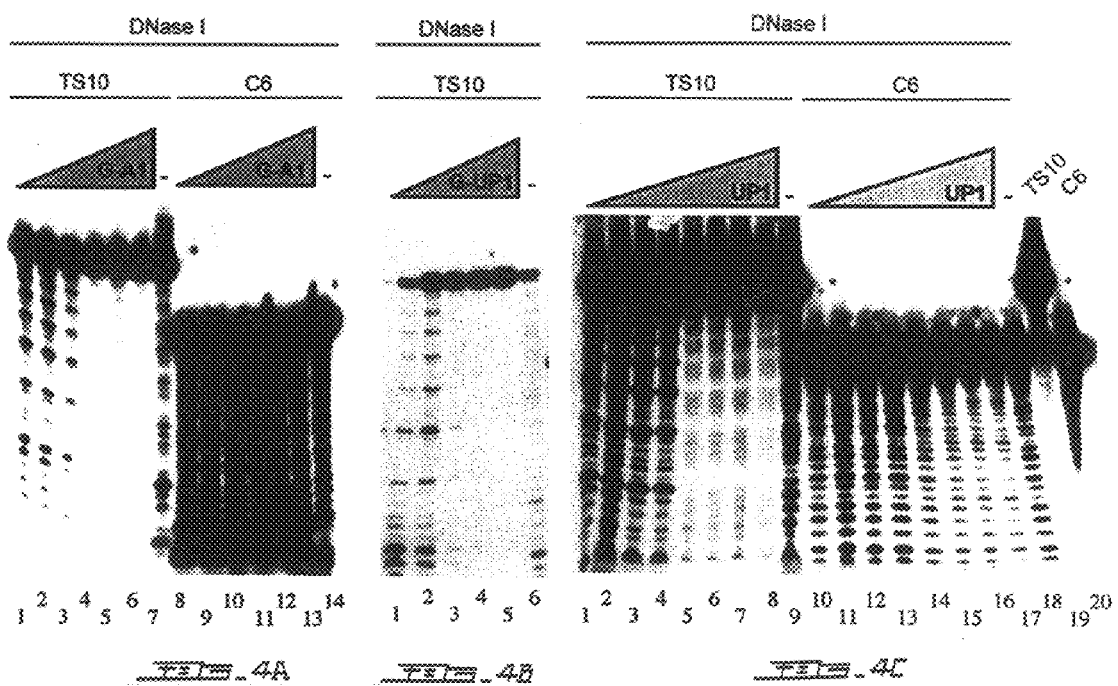
FIG. 4 shows that A1 and UP1 protect telomeric sequences from nuclease attack in vitro. DNase I protection assays were performed with 0.03, 0.08, 0.16, 0.2, 0.3 and 0.9 $\mu$M of GST-A1 (panel A), 0.1, 0.2, 0.3, 0.4, 1.2 $\mu$M of GST-UP1 (panel B) or 0.2, 0.45, 0.7, 0.9, 2.25, 3.4, 4.5 and 5.6 $\mu$M of UP1 (panel C). 0.1 $\mu$M of TS10 or C6 were used in each assay. The amount of DNase I used in panel B was higher than in panels A and C. D, DNase I protection assays were performed on TS10 with 0.1, 0.5 and 1.0 $\mu$M of UP1, UP1Δ1 and UP1Δ2 (GST derivatives). E, UP1 protects telomeric sequences from exonuclease I attack. The protection assay was performed with 0.1 $\mu$M of TS10 or C6 oligonucleotide at UP1 concentrations of 0.2 and 0.45 $\mu$M. F, UP1 binding protects telomeric sequences from Bal31 digestion. The graph represents the extent of protection from Bal31 (abscissa) relative to the percentage of input telomeric oligo bound by UP1 (ordinate).

Next, it was examined whether UP1 binding could protect telomeric sequences against nucleolytic activities. Incubation of naked TS10 with DNase I yielded a profile indicative of preferential cleavage after each G in every repeat (FIG. 4A, lane 7; FIG. 4B, lane 6 and FIG. 4C, lane 9). The sites of cleavage were confirmed by comparison to a profile obtained by DMS treatment which generates cuts at all G's (data not shown). At the lowest concentrations of GST-A1, DNase I cleavage occurred preferentially at the T↓T of each repeat (FIG. 4A, lanes 1–3). Complete protection of TS10 was observed at higher concentrations of GST-A1 (lanes 4–6). An assay performed with GST-UP1 and higher level of DNase I yielded similar results (FIG. 4B). Likewise, a preparation of UP1 lacking the GST moiety offered a level of protection that was equivalent to the level obtained with GST derivatives (FIG. 4C, lanes 1–8). In contrast, incubation of GST-A1 or UP1 with an oligonucleotide (C6) not bound by these proteins offered little or no protection against DNase I (FIG. 4A, lanes 8–14; FIG. 4C, lanes 10–18). Thus, low concentrations of A1 or UP1 changed the cleavage profile obtained with DNase I, consistent with the notion that TAGGGT is the unit bound by A1 and UP1. At high concentrations of A1 or UP1, complete protection was observed. The binding of A1 and UP1 to single-stranded telomeric sequences can therefore promote the assembly of a complex that is highly resistant to endonuclease attack. The derivative UP1Δ1, which binds weakly to TS10, did not offer significant protection against DNase I (FIG. 4D, lanes 8–10). Although UP1Δ2 binds to TS10 nearly as efficiently as UP1, it was less efficient at protecting TS10 against DNase I (FIG. 4D, lanes 5–7). Thus, strong binding is not sufficient to confer full protection, suggesting that portions of UP1 help prevent access of the endonuclease to DNA.

Protection assays were also performed with the E. coli 3' exonuclease I, which carries out nucleotide removal on naked TS10 or C6 to yield a ladder of products (FIG. 4E, lanes 3 and 6). It is unclear why no product shorter then ~35 nt was detected with TS10. The highest concentration of UP1 decreased the level of TS10 Exo I products by 2-fold while providing no protection to the C6 oligo (lanes 2 and 5, respectively). A similar experiment preformed with Bal31 exonuclease showed that the addition of increasing amounts of UP1 protects oligonucleotide TS10 but not C6 against Bal31 activity (data not shown). The efficiency of UP1 binding to the oligonucleotides correlated well with the level of protection from Bal31 (FIG. 4F). The results clearly indicate that UP1 binding to a long telomeric substrate provides protection against the activity of endo- and exo- nucleases.

A1 and UP1 Inhibit Telomerase-Mediated Extension

It was then investigated whether A1 or UP1 could affect the ability of telomerase to extend telomeric DNA in vitro. Recombinant UP1 lacking the GST moiety was pre-bound to TS10 and the complex was incubated in a HeLa S100 extract. In this conventional telomerase assay, the extension products are monitored directly following fractionation in a denaturing gel. In the absence of UP1, telomerase added multiple repeats to TS10 indicative of high processivity (FIG. 5A, lane 1). No activity was detected when the S100 extract was treated with RNase A (lane 2). Pre-incubation with increasing amounts of UP1 led to a gradual reduction in telomerase activity (lanes 3–5) such that few products were made at concentrations of UP1 that shifted TS10 into low mobility complexes (FIG. 5B, lanes 1–4). A similar result was obtained with GST-A1 (FIG. 5A, lanes 6–8). Inhibition appeared to be A1/UP1 protein-specific since pre-incubation with the single-stranded DNA binding gene 32 protein (gp32) was less efficient at inhibiting telomerase (FIG. 5A, lanes 9–11) despite the fact that gp32 assembled TS10 into low-mobility complexes as efficiently as UP1 (FIG. 5B, lanes 5–7).

Inhibition of telomerase activity by UP1 was less apparent when a short substrate was used. The appearance of the shorter extension products derived from oligonucleotide TS was not compromised by large amounts of UP1 (FIG. 5C, lane 2). However, UP1 promoted a small but reproducible decrease in the appearance of the largest (+20) extension product (lane 3). While oligonucleotide TS is a common substrate in telomerase (TRAP) assays, it does not contain a complete telomeric repeat and is not bound by UP1 (not shown). Because the largest TS extension product carries 3 complete A1 binding sites (TAGGGT), the product carrying two sites is therefore the first substrate sensitive to the addition of UP1. This is consistent with our observation that at least two TAGGGT units are required for stable UP1 binding. A derivative carrying one complete telomeric repeat (TS1) was also tested. While TS1 can be extended in a S100 extract, the addition of UP1 compromised the appearance of a shorter (+14) extension product (FIG. 5C, lane 4), again consistent with the notion that at least two TAGGGT units are required for UP1 binding.

To confirm that UP1 binding to the telomerase substrate was responsible for the inhibition, UP1 was pre-incubated with a molar excess of an oligonucleotide bound by UP1 (TS8A), or an oligonucleotide not bound by UP1 (MS2). TS8A and MS2 are not efficiently extended by telomerase (data not shown). Pre-incubating UP1 with TS8A stimulated extension of TS10 (FIG. 5D, lanes 3 and 4), while pre-incubation with MS2 had little effect (lanes 5 and 6). Overall, these results show that inhibition of telomerase activity by UP1 is specific to substrates carrying high-affinity A1 binding sites.

The inhibitory activity of UP1 derivatives lacking either RRM1 or RRM2 was also tested. Although UP1Δ2 binds to TS10 as efficiently as the complete UP1 protein, it did not inhibit telomerase extension of TS10 (FIG. 5E). UP1Δ1, which does not bind efficiently to TS10, also did not affect telomerase extension (data not shown).

UP1 Inhibits the Activity of Other DNA Polymerases

To ask whether UP1 could affect the activity of other DNA polymerases, the activity of calf thymus terminal deoxynucleotidyltransferase (TdT), which like telomerase carries out extension on a 3' end was first tested. Unlabeled TS10 oligomer was incubated with TdT in the presence of UP1 and radiolabeled TTP. Nucleotide addition was monitored on a denaturing polyacrylamide gel. As shown in FIG. 6, UP1 strongly inhibited extension of TS10 (lanes 2–4). UP1Δ2 also efficiently repressed TdT activity (lanes 5–7), while UP1Δ1 had little effect (lanes 8–10). The inhibitory effect of UP1 was specific since an oligonucleotide lacking an A1 binding site (TS oligo) was efficiently extended by TdT in the presence of high concentration of UP1 (data not shown). Notably, the addition of gp32 also prevented extension of TS10 by TdT (lanes 11–14). Thus, although UP1Δ2 and gp32 were poor inhibitors of telomerase, both could prevent TdT access to the substrate. These results suggest that the mechanism by which UP1 inhibits telomerase is different from the mechanism that inhibits TdT.

Figures 7A, 7B:
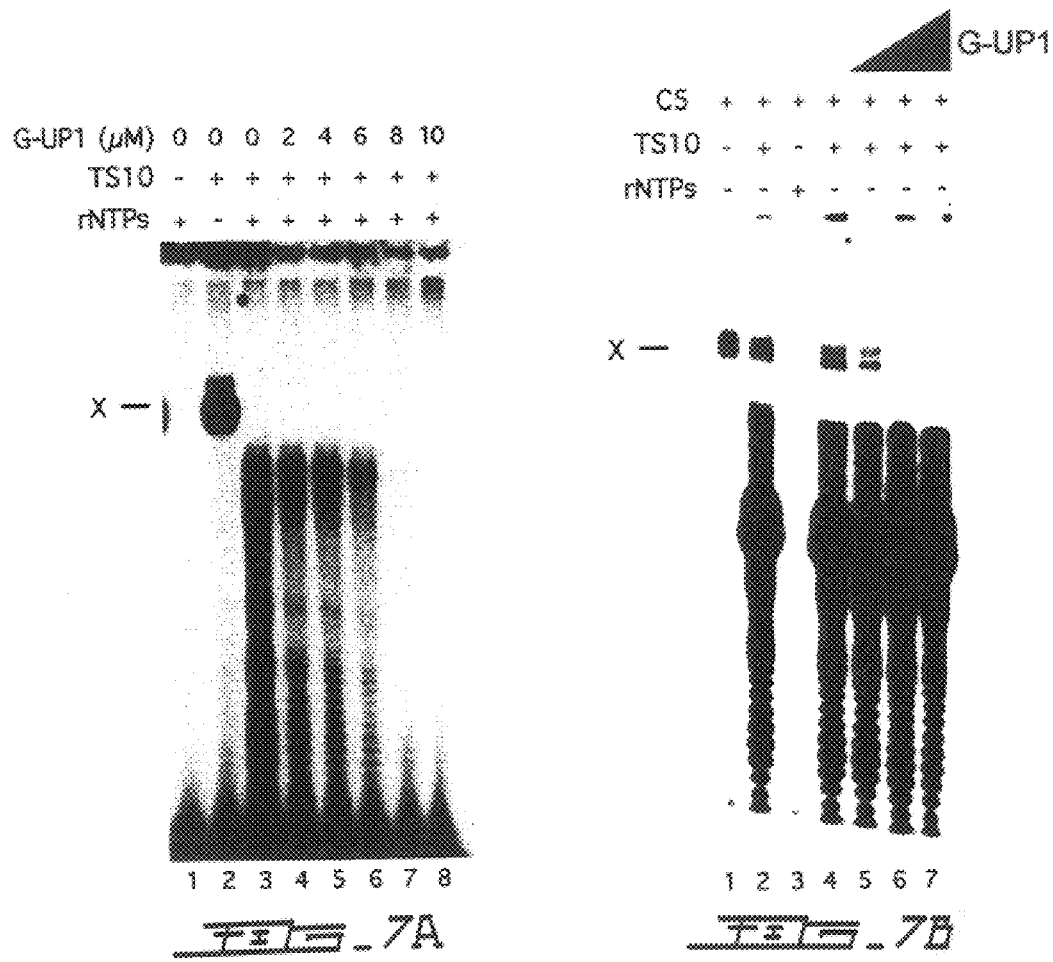
FIG. 7 shows that UP1 inhibits rNTP-dependent lagging-strand synthesis. A, the lagging-strand synthesis assay was performed with TS10 (0.5 $\mu$M) in the absence of dGTPs and rGTP. rNTPs=UTP, rCTP, rATP. The band identified as X (also seen in panels B and C) is of unknown origin but was always seen when TS10 was incubated in the absence of rNTPs. B, UP1 does not inhibit rNTP-independent lagging-strand synthesis. In addition to TS10 (0.5 $\mu$M), the mixture contained an oligonucleotide complementary to TS10 (C5, 1 $\mu$M) and dNTPs (dCTP, dATP and dTTP). In this experiment, the highest amount of GST-UP1 used completely inhibited rNTP-dependent lagging-strand synthesis (data not shown). C, rescue of rNTP-dependent lagging-strand synthesis by oligonucleotides. In the assay shown in lanes 1–7, the amount of TS10 was increased while keeping the concentration of UP1 constant. In the assay shown in lanes 8–14, oligonucleotides Tel2 and Ne4 were co-incubated with TS10 in the HeLa extract without exogenous UP1. Tel2, but not Ne4, is bound by UP1 in gel-shift assays (not shown). The assay depicted in lanes 15–20 monitors the effect of co-incubating oligonucleotide Tel2 in a HeLa nuclear extract (HeLa), a HeLa S100 extract (S100) and a nuclear extract prepared from mouse erythroleukemic CB3 cells that is severely deficient in hnRNP A1 protein. Endogenous levels of A1 are high in HeLa and low in S100.

Purified UP1 was reported to stimulate the activity of DNA polymerase a when poly dA/dT is used as substrate (Riva et al., 1986, EMBO J. 5:2267). To determine whether UP1 displays a similar activity on a telomeric substrate, an in vitro assay to monitor the synthesis of the mammalian telomere lagging-strand was used. Using TS10 as DNA template, DNA polymerase α/primase was shown to catalyze synthesis of the complementary strand, a process that required both dNTPs and rNTPs (Reveal et al. 1997, supra). In agreement with this report, it was observed that incubation of unlabeled TS10 in a HeLa nuclear extract leads to the synthesis of products shorter than 60 nt (FIG. 7A, lane 3). Synthesis required rNTPs and dNTPs but omission of GTP and/or rGTP did not affect the appearance of labeled products (lane 2, and data not shown). The rNTP-dependence of the assay is indicative of DNA polymerase α/primase activity. When the complementary oligonucleotide C5 was pre-incubated with TS10, lagging-strand synthesis occurred in the absence of rNTPs, suggesting DNA polymerase δ and/or ε activity (FIG. 7B, lane 2). To confirm that the rNTP-dependent activity was mediated by DNA polymerase α/primase, the inhibitory effect of a monoclonal antibody specific for DNA polymerase α/primase was tested. The SJK 132–20 antibody completely inhibited rNTP-dependent DNA synthesis but did not affect rNTP-independent DNA synthesis (data not shown).

Notably, the addition of increasing amounts of GST-UP1 inhibited rNTP-dependent synthesis in the HeLa nuclear extract (FIG. 7A, lanes 5–8), but did not affect rNTP-independent synthesis (FIG. 7B, lanes 4–7). Inhibition was also seen with UP1, GST-A1 and commercial preparations of SSB and gp32 proteins (data not shown).

It is unlikely that the protein preparations used contain a non-specific inhibitor of DNA polymerase α/primase activity since increasing the amounts of TS10 in mixtures containing UP1 stimulated lagging-strand synthesis (FIG. 7C, lanes 5–7). Consistent with this observation, the addition of a shorter telomeric oligonucleotide (Tel2) to a HeLa mixture containing TS10, but not recombinant UP1, also stimulated rNTP-dependent lagging-strand synthesis (FIG. 7C, compare lane 12 with lane 13). In contrast, the addition of a control oligonucleotide lacking telomeric sequences did not stimulate lagging-strand synthesis (lane 14). These results suggest that Tel2 can specifically suppress the inhibition caused by nuclear factor that binds to TS10. Given that recombinant A1 protein also inhibits lagging-strand synthesis, endogenous A1 proteins are likely repressing lagging-strand activity in the HeLa extract. This conclusion is supported by the following experiment in which rNTP-dependent activity was monitored in a HeLa nuclear extract, a HeLa post-nuclear S100 extract, which contains residual levels of hnRNP A1, and a nuclear extract prepared from a mouse cell line (CB3), which is severely deficient in hnRNP A1. Compared with the strong stimulation obtained when Tel2 is added to the HeLa nuclear extract (FIG. 7C, compare lane 15 with lane 18), Tel2 only had a modest stimulatory effect when added to the HeLa S100 (compare lane 17 with lane 20), and no effect when added to the CB3 extract (compare lane 16 with lane 19). These results indicate that endogenous A1 proteins repress lagging-strand synthesis in the HeLa nuclear extract, and that sequestration of A1 by Tel2 considerably improves rNTP-dependent synthesis on TS10.

Inhibition of lagging-strand synthesis could also be obtained with UP1Δ2 but not with UP1Δ1 (data not shown). Thus, the mechanism by which UP1 inhibits lagging-strand synthesis and TdT activity may be similar, but distinct from the mechanism by which UP1 prevents telomerase extension.

It had been shown previously that hnRNP A1 and its shortened derivative UP1 can promote telomere elongation in mammalian cells (WO 98/00537). The ability of A1 and UP1 to bind specifically to single-stranded telomeric repeats suggests that A1 may interact with telomeric extensions at the ends of mammalian chromosomes. In addition, recombinant UP1 but not recombinant A1 protein can recover telomerase activity from a cell extract. Because a proteolytic activity that produces UP1 from A1 has been reported, this conversion may represent an important step in the production of a factor that can interact with telomerase. Aternatively, post-translational modifications occurring at the C-terminal glycine-rich domain of A1 may modulate the interaction with telomerase. These possibilities are currently being investigated. Herein, the effect of recombinant A1 and UP1 on a variety of processes that are relevant to telomere biogenesis has been addressed. It is herein shown that the binding of A1 or UP1 protects a single-stranded telomeric substrate against the activity of endo- and exonucleases. Moreover, recombinant A1 and UP1 proteins prevent telomerase extension and telomere replication by DNA polymerase α/primase in vitro.

Interaction of A1/UP1 with Telomeric Repeats

A UP1 derivative lacking RRM2 binds to a telomeric oligonucleotide with an affinity and specificity that are nearly equivalent to the complete UP1 protein. In contrast, deleting part of RRM1 severely compromises binding. Thus, while the RRM1 domain is essential for binding, the RRM2 domain appears dispensable therefor. This conclusion contrasts with a previous observation indicating that both RRM1 and RRM2 are required to recover molecules carrying RNA versions of telomeric repeats from a pool of random sequence (Burd and Dreyfuss, 1994, EMBO J 13:1197). Because these experiments were performed with derivatives carrying the C-terminal glycine-rich domain, it is possible that this domain affects the binding properties of the preceding RRM. The deletion of RRM2 in A1 would position the glycine-rich domain next to RRM1 and could alter its binding specificity. Because the glycine-rich domain is absent from UP1, the deletion of RRM2 would maintain the binding specificity of RRM1 in the assays used. Thus, while cooperativity between RRMs has been assumed to be a general property of proteins with multiple RRMs, the present result clearly show that RRM2 is not required for strong and specific binding to telomeric oligonucleotides. Because at least two TAGGGT repeats are required for the assembly of a stable complex with A1 or UP1, the results of the present invention suggest that a minimal complex involves two A1 or two UP1 molecules, each protein using only RRM1 to bind to one repeat unit. The recent X-ray structure of UP1 bound to 12 nt of telomeric DNA indicates that UP1 binds as a dimer to two strands of telomeric DNA, the RRM1 and RRM2 of one UP1 monomer binding to separate strands (Ding et al., 1999, Genes Dev 13:1102). Whereas each telomeric repeat is contacted by only one RRM, RRM1 and the adjacent linker region make more contacts with the bases of a telomeric repeat than RRM2, suggesting that the N-terminal half of UP1 plays a dominant role in the affinity and/or specificity of binding. In contrast to the work of Ding et al., the results presented herein suggest that UP1 does not simultaneously interact with different strands since the incubation of UP1 with two small telomeric oligos of different lengths does not lead to the assembly of complexes containing both oligos.

A Role for A1/UP1 in the Maintenance of a Telomeric 3' Overhang

Maintaining the integrity of telomeric 3' overhangs is paramount to telomere function. In mammals, this conclusion is supported by recent studies performed with TRF2, a protein that binds to double-stranded telomeric repeats. Overexpression of a dominant negative variant of TRF2 promotes the loss of 3' overhangs, an event associated with chromosome fusions and apoptosis (van Steensel et al. 1998, Cell 92:401; Karlseder et al. 1999, Science 283:1321). Consistent with the properties expected for a protein that binds to 3' overhangs, A1/UP1 displays specific binding to mammalian telomeric repeats, and prefers binding to telomeric sequences that are located at the 3' terminus of an oligonucleotide. While specific binding is also a property of the telomere single-stranded binding proteins of Oxytricha and Euplotes, the yeast Cdc13p/Est4p and Est1p proteins can interact, albeit with reduced affinity, to vertebrate and ciliate telomeric sequences (Price et al., 1992, Biochemistry 31:10835). The Oxytricha and Euplotes proteins that bind to single-strand telomeric repeats protect telomeric DNA from nuclease digestion (Price, 1990, Mol Cell Biol 10:3421). Likewise, the interaction of A1/UP1 with vertebrate telomeric single-stranded DNA confers resistance against the activity of both endo- and exonucleases. Thus, the ability of A1/UP1 to protect telomeric repeats from nuclease attack suggests that A1 UP1 may be an important component of the protective cap associated with telomere function. Although a recent study suggests that mammalian telomeric 3' overhangs may be sequestered in duplex loops (Griffith et al., 1999, Cell 97:503), the internal G-rich single-stranded regions created by the formation of such structures may also require protection from nucleases. As A1/UP1 binding also prevents access to telomerase, to TdT and inhibits rNTP-dependent DNA synthesis, the binding of A1/UP1 may help shield the ends of chromosomes from surveillance mechanisms that detect DNA damage and double-stranded breaks.

Figure 8:
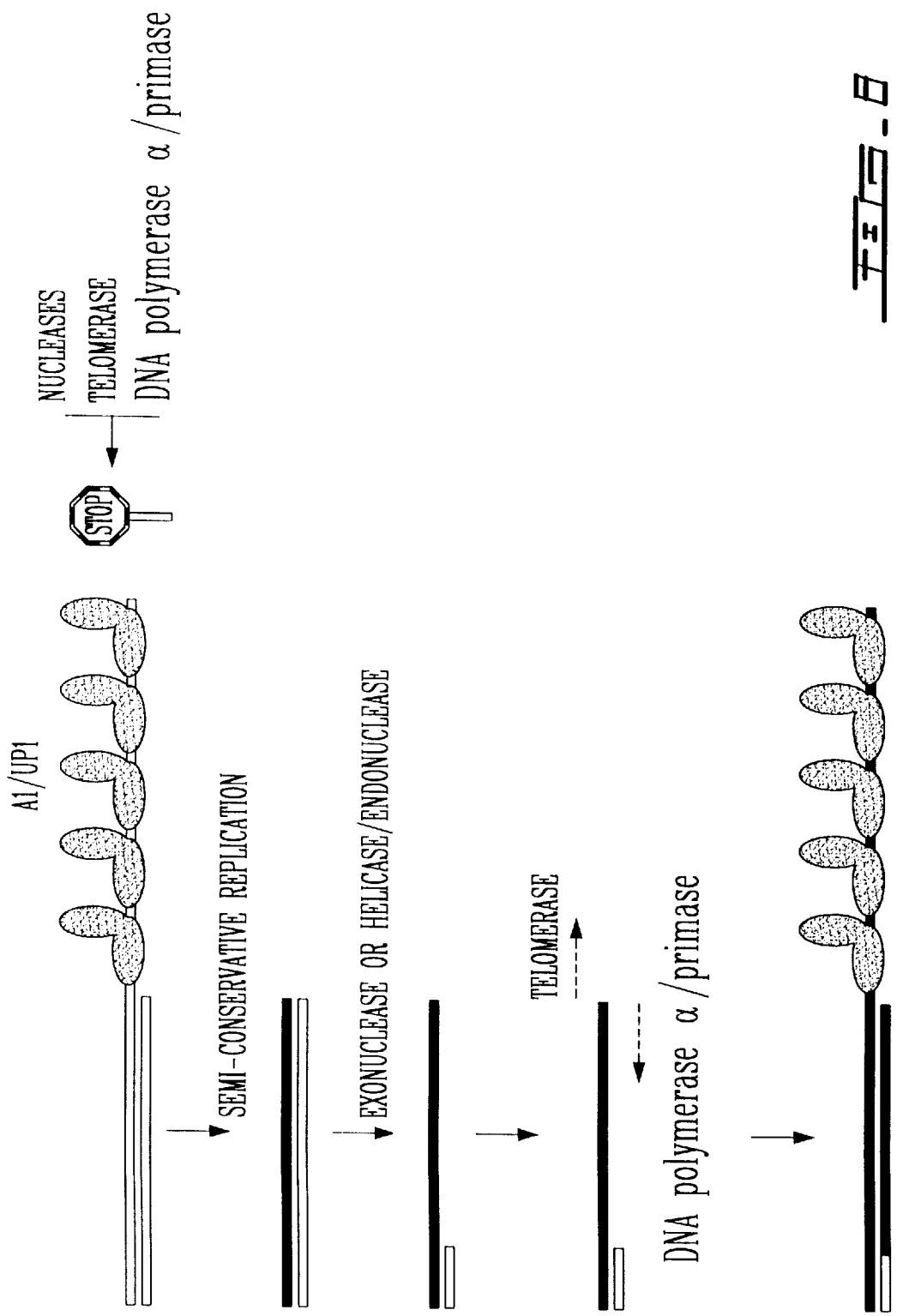
FIG. 8 shows a model for the role of A1/UP1 in telomere biogenesis. At the top, several A1/UP1 molecules are shown to interact with a single-stranded telomeric extension. A1/UP1 binding would prevent access of enzymes to the 3' overhang, thereby protecting the structure and preventing its recognition as DNA damage. Following telomere replication by conventional DNA polymerases, a putative exonuclease or endonuclease/helicase complex would produce a 3' overhang from the newly synthesized DNA strand (black bar). This overhang may serve as substrate for telomerase and lagging-strand synthesis until the nascent extension becomes bound by A1/UP1.

In addition to functioning as protective caps, telomeres also facilitate the complete replication of chromosomes. The enzyme telomerase plays a crucial role in this process by extending the 3' end of the G-rich strand. It is shown herein that the binding of A1/UP1 to single-stranded telomeric repeats prevents telomerase extension in vitro. The Oxytricha telomere DNA binding proteins also attenuate telomerase extension in vitro. The ability of A1/UP1 to promote telomere elongation despite causing telomerase repression in vitro may indicate that A1/UP1 functions predominantly by favoring the assembly of a protective cap at the ends of chromosomes. Thus, the repression of synthetic activities would be an indication of the insulating property of A1/UP1. Given that A1/UP1 binding prevents extension by telomerase, the interaction between UP1 and telomerase in vitro may reflect the ability of UP1 to recruit telomerase as part of the assembly of a protective cap. In support of this model, the stable interaction of yeast telomerase with single-stranded telomeric repeats was taken to suggest that telomerase might be a component of the telomere cap (Prescott and Blackburn, 1997, Genes Dev 11:2790). While the binding of A1/UP1 to single-stranded telomeric repeats prevents access to a variety of replication enzymes, it is likely that telomerase must gain access to a 3' overhang at some point during the replication cycle. Without being limited to one particular model, it is proposed that following conventional DNA replication and the activity of specific nucleases (FIG. 8), the newly formed 3' overhang may remain free of A1/UP1 for a sufficient time to allow extension by telomerase and partial filling by DNA polymerase α/primase. The subsequent binding of A1/UP1 to newly made telomeric tails would help maintain long 3' overhangs throughout the rest of the cell cycle.

In conclusion, the results shown herein indicate that the binding of A1/UP1 to single-stranded telomeric sequences provides protection against nucleolytic activities. A1/UP1 binding also renders the 3' end of a telomeric substrate inaccessible to a variety of polymerases. The present invention thus provides the means to begin to envision how the protective and replication-modulating activities associated with the binding of A1/UP1 contribute to telomere biogenesis in mammalian cells. The invention further provides the means to further dissect the structure function relationship of A1/UP1, its interaction with telomeres and telomerase and the effect thereof on telomere biogenesis.

In order to further dissect the role for A1/UP1 in promoting telomere elongation through its interaction with telomeric sequences in vitro, and the recovering of telomerase activity from a cell extract, a number of experiments using recombinant UP1 protein were performed. These lead to the showing that A1/UP1 interacts directly and specifically with the RNA component of human telomerase (hTR). While the first half of UP1 which contains RRM1 is sufficient for binding to a telomeric DNA oligonucleotide, the second half of UP1 which contains RRM2 can interact specifically with the 5' half of hTR. Moreover, evidence is provided for the existence of a ternary complex made up of telomeric sequences, A1/UP1 and hTR. The fact that these interactions resist incubation in a cell extract argues in favor of their biological relevance. These results provide the first example of a protein that can interact simultaneously with DNA and RNA, and suggest that one function of A1/UP1 may be to recruit telomerase to the ends of chromosomes.

HnRNP A1 is one of the most abundant nuclear protein in actively growing mammalian cells. A1 is involved in a variety of RNA-related processes including alternative RNA splicing and mRNA transport. More recently, it has been reported that a deficiency in A1 expression in a mouse erythroleukemic cell line is associated with short telomeres, and that restoring A1 expression increases telomere length. The expression of a shortened version of A1 (UP1), which is inactive in alternative splicing, can also promote telomere elongation in mouse and human cells, Although the binding of A1/UP1 to telomeric 3' overhangs in vivo remains to be shown, the evidence strongly suggests that the effect of A1/UP1 on telomeres is mediated by the direct binding ot A1 to single-stranded extensions (as shown above). The evidence provided herein also strongly suggests that the in vitro results will be observed in vivo.

In view of further understanding the mechanisms implicated in telomere biogenesis, the RNA binding ability of A1/UP1 was analyzed. A1/UP1 can interact directly with hTR, the RNA component of telomerase. Moreover, this interaction is specific and requires RRM2. The surprising finding that the interaction between A1/UP1 and hTR can occur while A1/UP1 simultaneously binds to single-stranded telomeric sequences suggests that another function of A1/UP1 may be to recruit telomerase at the ends of chromosomes.

UP1 Interacts Specifically with Human Telomerase RNA

Figure 9A:
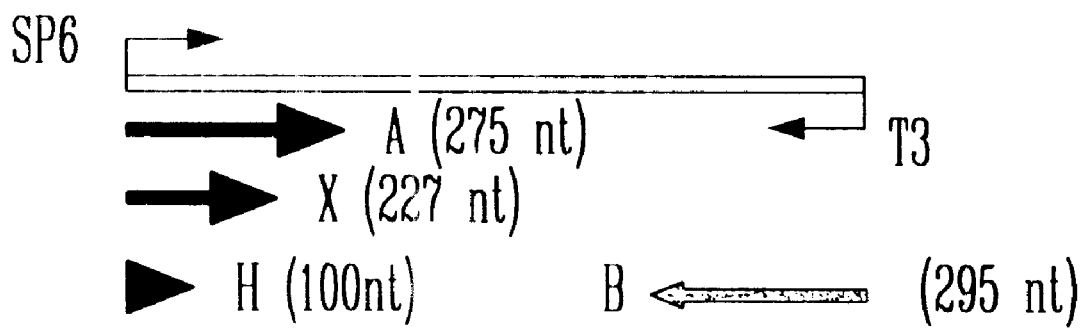
FIG. 9 shows that UP1 binds specifically to hTR. (A) Substrates used in gel-shift assays. Below hTR are illustrated various transcripts made by SP6 and T3 RNA polymerase (B) UP1 binding assay. (C) UP1 binding in the presence of competitor RNAs. UP1 (5 pmoles) and the $^{32}$P-labeled RNA were incubated in the presence of increasing amounts of unlabeled hTR-A RNA or hTR-B. Because the unlabeled RNAs were synthesized in the presence of residual amounts of $^{32}$P-UTP to facilitate purification, aliquots of unlabeled hTR-A and hTR-B are shown as controls (lanes 9 and 14, respectively).
Figure 9B:
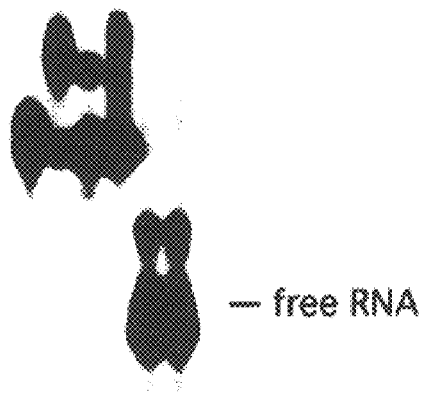

To test whether UP1 can interact directly with telomerase RNA, a gel mobility shift assay was performed using a recombinant UP1 protein produced in E. coli and carrying a GST moiety. As substrate, an in vitro transcribed $^{32}$P-labeled human telomerase RNA (hTR) was used. A battery of shorter forms of hTR that were produced by run-off transcription of phTR DNA linearized at internal positions (FIG. 9A) was also tested. For control RNAs, a variety of RNAs were used, one of which carried 295 nt of sequences that are complementary to the 3' end of hTR. The results of the gel-shift assays are shown in FIG. 9B. These results indicate that UP1 can bind in a substrate-specific manner to the 5' end portion of hTR. The shortest RNA that is bound specifically by UP1 contains the first 227 nt of hTR, suggesting that the binding site includes the template region.

Figure 9C:
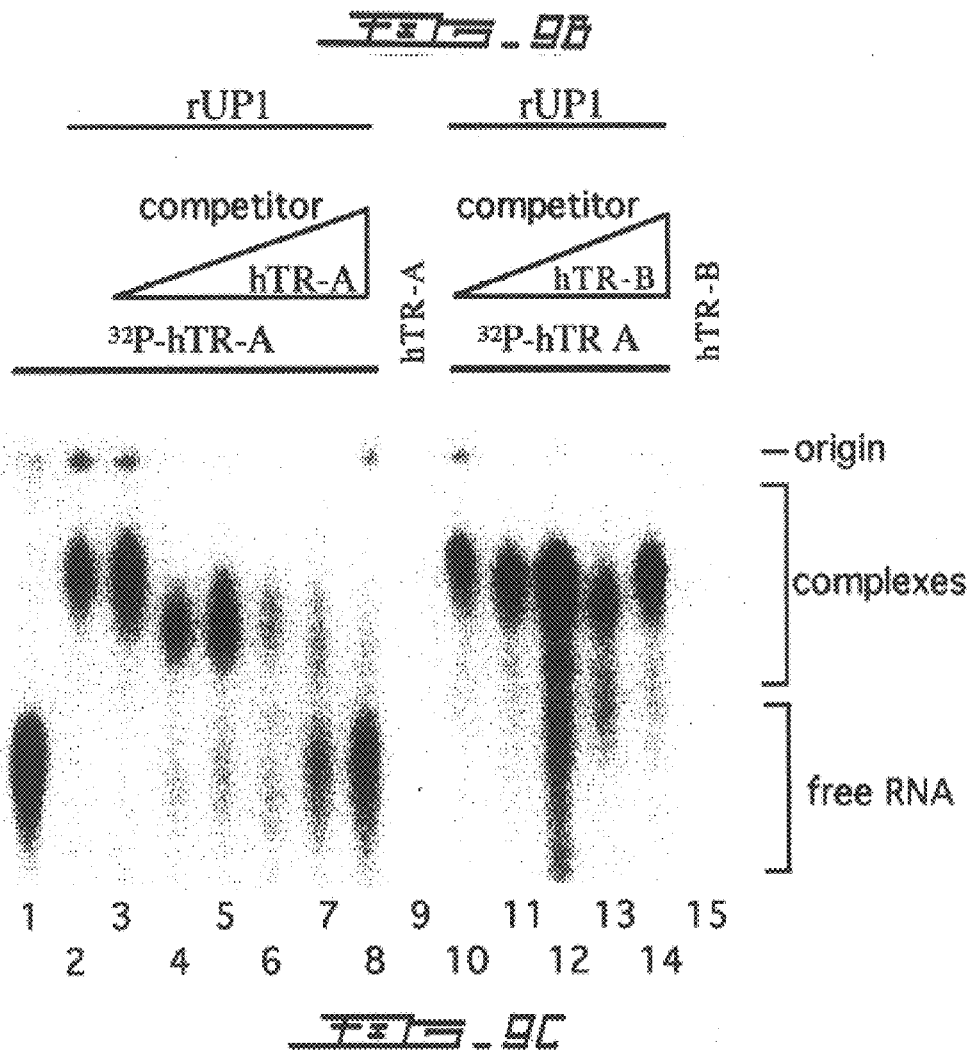

To address further the binding specificity of UP1, the binding assay was performed in the presence of competitor RNAs. As shown in FIG. 9C, a gradual increase in the amount of unlabeled hTR-A RNA eliminated the assembly of UP1/$^{32}$P-hTR-A complexes (lanes 1–8). In contrast, these complexes were not affected by similar amounts of unlabeled hTR-B RNA (lanes 10–14).

It has been reported that UP1, but not the full-length hnRNP A1 protein, could recover telomerase activity from a mammalian extract. The interaction of recombinant hnRNP A1 protein with hTR-A RNA was assessed. It was expected that A1 would fail to interact with hTR-A RNA. Initially, it was observed, as expected, that the recombinant A1 protein (rA1) interacted much less efficiently with hTR-A than UP1 (FIG. 10, left panel), despite the fact that both proteins interacted with similar efficiencies to the telomeric oligonucleotide TS10 (not shown). However, during the course of these investigations, a modified procedure for the preparation of recombinant proteins (Procedure II) was used (see Example 9). This procedure allowed the obtention of a much better yield of rA1 with reduced amounts of shorter products. Surprisingly, rA1 preparations made according to procedure II interacted with hTR-A RNA as efficiently as UP1 (FIG. 10, right panel). These results indicate that both rA1 and rUP1 can interact with telomerase RNA. The failure of early A1 preparations to interact with hTR may be due to an improper folding of the glycine-rich domain, a region that has been reported to be largely unstructured, and thus possibly more prone to interfere with the activity of a nearby nucleic acid binding motif.

RRM2 is Required for the UP1/hTR Interaction

Using TS10 as the substrate oligonucleotide, the first half of the UP1 protein, the portion that contains RRM1 and the linker region, was found to be sufficient for strong and specific binding to TS10, as judged by gel-shift assays. To determine the contribution of each region in binding to hTR, a gel-shift assay with two UP1 derivatives, UP1Δ1 and UP1Δ2 was performed. UP1Δ1 lacks most of RRM1 while UP1Δ2 lacks RRM2 (FIG. 11A). Interestingly, while UP1Δ1 was able to form a complex with hTR-A (FIG. 11B, lane 2), UP1Δ2 was not (lane 3). The interaction of UP1Δ1 with hTR-A was specific since no complex was formed when UP1Δ1 was incubated with hTR-B (lane 4). These results suggest that the two RRM of hnRNP A1 have distinct functions; RRM1 binds telomeric DNA sequences while RRM2 binds the RNA component of telomerase.

If the binding to telomeric DNA and telomerase RNA occurs through distinct RRMs, an excess of one nucleic acid (telomeric DNA) should not interfere with the binding of UP1 to the other nucleic acid (telomerase RNA). Consistent with this prediction, the binding of UP1 to $^{32}$P-hTR-A remained relatively insensitive to a gradual increase in the amounts of the telomeric oligonucleotide TS10 (FIG. 11C, lanes 3–8). While TS10 promoted a small dissociation of hTR-A (FIG. 11C, lanes 7 and 8), similar amounts of competitor hTR-A led to a complete disruption of UP1/$^{32}$P-hTR-A complexes (FIG. 9C, lanes 7 and 8). These results therefore strongly support the notion that the two nucleic-acid binding domains of A1/UP1 can bind to different molecules. However, these results do not address whether UP1 can interact simultaneously with telomeric DNA and telomerase RNA. Indeed in the system used, the migration of a complex is determined more by the size/number of proteins than the length/number of nucleic acids. Thus, the binding of a 60 nt DNA oligo to a UP1 molecule already bound to a 223 nt RNA would only have a minor effect on the migration.

A1/UP1 can Interact Simultaneously with hTR RNA and Telomeric Sequences

Figure 12A:
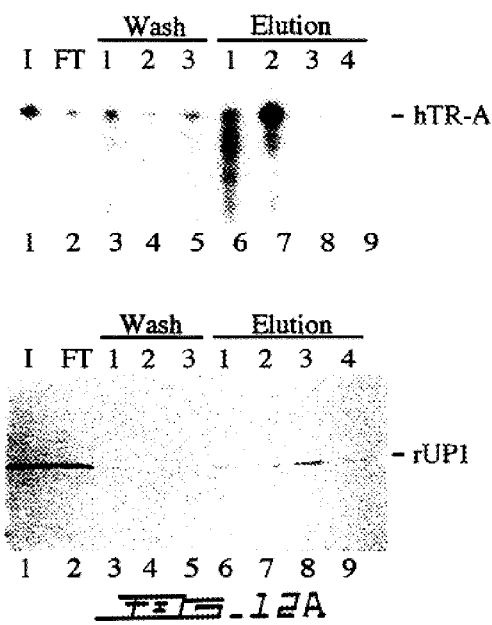
FIG. 12 shows that A1 and UP1 interact simultaneously with telomeric DNA sequences and the RNA component of telomerase. Various mixtures of $^{32}$P-hTR-A and proteins were loaded onto TS10 columns. The top portion of panels A to C are acrylamide/urea gels exposed to visualize $^{32}$P-labeled hTR-A in various fractions, while the bottom portion of panels A to C represents protein gels stained with Coomassie blue. Panels D is an acrylamide/urea gel exposed to visualize $^{32}$P-labeled hTR-A after loading to the TS10 column in the absence of protein. Panel E is a protein gel stained to visualize the elution profile of rUP1 and GST. I=Input ($\frac{1}{10}^{th}$ of total fraction), FT=flow-through fraction ($\frac{1}{10}^{th}$ of total fraction). Wash 1, 2 and 3 are successive washes with loading buffer (buffer DN). Elution 1, 2, 3 and 4 are successive elutions with buffer DN containing 250 mM, 500 mM, 750 mM and 1M NaCl, respectively. M=protein molecular weight markers. The position of the proteins and hTR-A is indicated.
Figure 12B:
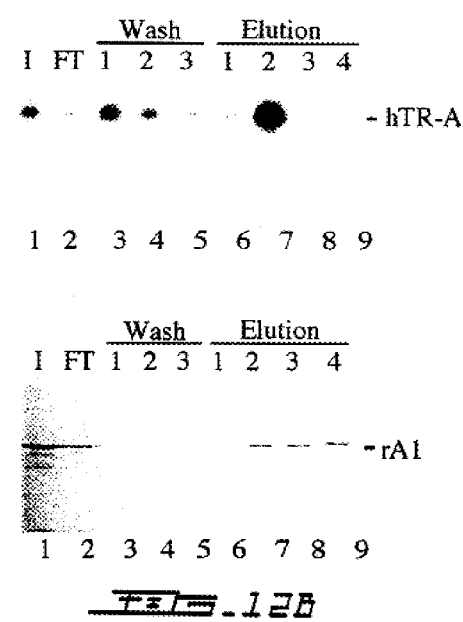

The ability of A1/UP1 to interact with telomeric sequences through the RRM1 domain and to interact with telomerase RNA through the RRM2 domain raises the possibility that these interaction occur simultaneously on the same UP1 molecule. To address whether A1/UP1 could form a ternary complex with telomeric sequences and hTR RNA, the following experiment was performed. TS10 oligonucleotides were covalently coupled to an adipic acid hydrazide agarose column. The column was then incubated with a preparation containing $^{32}$P-labeled hTR-A RNA and rUP1. Control incubations were also performed with labeled hTR-A RNA and rA1 or the procaryotic gene 32 protein (gp32). The columns were then washed extensively first with loading buffer and then at increasing salt concentrations to elute bound complexes. In the absence of protein, the labeled RNA was not significantly retained by the column, as noted by the presence of hTR-A in the flow-through fraction only (FIG. 12D). In contrast, in the presence of rUP1 and rA1, the RNA/protein complex was retained on the column, labeled hTR-A eluting majoritarily in the 0.5M NaCl fraction (panels E and F, respectively). The bulk of bound rUP1 and rA1 also started eluting at 0.5M NaCl (panels A and B, respectively). The fact that no RNA remained in the 0.75M NaCl fraction which still contains rA1 indicates that the RNA-protein interaction is resistant to NaCl concentrations of up to 0.5M. Although gp32 can bind telomeric oligonucleotides, as judged by gel-shift assay, gp32 was not retained by the TS10 column (panel C), nor could gp32 promote the retention of hTR-A RNA to the TS10 column (panel G). These results indicate the existence of a ternary complex involving A1/UP1, telomerase RNA and telomeric DNA.

It has been shown in another study using adipic acid columns that rA1 can interact with itself. However, this interaction requires the glycine-rich domain and does not occur with rUP1. Thus, it is believed that the simultaneous interaction of A1/UP1 with telomerase RNA and telomeric DNA occurs on a single A1/UP1 molecule, rather than on a complex containing several A1/UP1 proteins in which one molecule would bind TS10 and another hTR-A. Consequently, rUP1-dependent binding of hTR-A to the TS10 column suggests that UP1 can interact simultaneously with the telomeric oligo and telomerase RNA.

The above experiments were performed with purified components in the absence of competitor RNAs or competitor proteins. To evaluate whether these interactions can occur in the context of a cell, the rUP1/hTR-A or rA1/hTR-A complexes were incubated in a concentrated HeLa extract that is normally used to carry out conventional telomerase assays (S100 extract). The mixture was then loaded onto the TS10 column to determine whether hTR-A could be retained in a rA1- or rUP1-dependent manner. The results shown in FIG. 13 indicate that the ternary complex (hTR-A/UP1/ TS10 or hTR-A/A1/TS10) can assemble in the context of the S100 extract. This result suggests that these interactions are sufficiently strong to occur in the cell nucleus and thus in vivo.

A1 and its shortened derivative UP1 have been shown to bind specifically to human telomerase RNA (hTR) in vitro. The first 275 nt (hTR-A) are sufficient for strong and specific binding. This region corresponds to the minimal region of hTR that can rescue telomerase activity in an extract where endogenous hTR had previously been inactivated by micrococcal nuclease digestion. Shorter versions of hTR indicate that the binding site may be located within the first 227 nt, a region that contains the template region. The mapping of the precise binding site of A1/UP1 on the 5' end of hTR awaits further analysis.

The present invention surprisingly shows that (1) the first nucleic acid binding domain of UP1 (RRM1) was sufficient for efficient binding to telomeric DNA sequences in vitro; (2) the second nucleic acid binding domain of UP1 (RRM2) was not essential for binding to telomeric sequences; (3) deletion of RRM1 did not affect binding to hTR; and (4) a derivative containing only the complete RRM2 was still capable of binding specifically to the 5' end portion of telomerase RNA.

These results indicate that each of the two RRMs of UP1 could independently bind distinct nucleic acid molecules. Most surprisingly, these interactions can occur simultaneously in vitro using purified components. Moreover, these interactions can resist incubation in a cell extract. Although some proteins have the ability to bind either DNA or RNA (e.g., gp32, ssB, TFIIIA), the fact that a protein can bind simultaneously to a DNA and a RNA molecule represents a unique situation that had yet to be described in a biological system.

Another feature of the investigation is the finding that hnRNP A1 can also interact with hTR, and maintain this interaction while binding simultaneously to telomeric sequences. The initial observation had indicated that A1, in contrast to UP1, did not recover telomerase activity from a cell extract. As shown here, these contradictory results can be reconciled by noting that the procedure used to prepare A1 proteins is determinant in conferring thereto the ability to bind the hTR. The procedure used in the initial report to yield A1 molecules that could not interact with hTR as efficiently as UP1, whereas the new procedure yielded A1 proteins that could efficiently interact with hTR. Although the reason for these differences remains unclear, it has been reported that the glycine-rich domain (GRD) of A1, absent from UP1, can be unstructured. One possibility is that the GRD can interfere with the binding activity of the closest RRM (RRM2) which has been shown to be involved in hTR binding. The second procedure of A1 purification may be less disruptive and may yield a more structured GRD, thereby maintaining the biological ability of RRM2 to interact with hTR. This initial observation had led to the suggestion that a conversion of A1 into UP1 might be an important event to yield a protein capable of interacting with telomerase. However, in light of the results presented herein, the model which is favored is based on the structure of the GRD domain and its modulation of the A1/hTR interaction. Post-translational modifications like phosphorylation of the GRD apparently affect the structure of the GRD. Since a number of kinases, including PKCζ, have been documented to phosphorylate GRD in vitro and in vivo, recruitment of telomerase to chromosome ends could be modulated through kinases that target A1. The demonstration above at least in vitro, that UP1 inhibits telomerase activity, an observation that has led to the postulation that the main role of A1 might be to recruit telomerase as part of the protective cap on telomeres.

The present invention is illustrated in further detail by the following non-limiting examples.

EXAMPLE 1

Oligonucleotides and Plasmids

DNA oligonucleotides (see Table I) were purified on acrylamide/urea gels. For binding assays, oligonucleotides were 5' end labeled by incubation with T4 polynucleotide kinase, and purified using MicroSpin™ G-25 columns. pGEX-A1 was constructed by inserting the mouse A1 cDNA into the EcoRI site of pGEX-2T. The expression plasmids PGEX-UP1 and pGEX-A1 were also described previously in LaBranche et al., 1998. The pGem-T plasmid encoding the human RNA telomerase component was kindly provided by S. Bacchetti and R. Reddel. The UP1 fragment was inserted into the EcoRI site of pGEX-2T. pGEX-UP1ΔRRM1 was produced by deleting the PvuII-NdeI fragment. pGEX-UP1ΔRRM2 was produced by cutting pGEX-UP1 with BglII, filling with Klenow before religation.

TABLE I

| | | |
|---|---|---|
| aT | GGCCTAGTGTCCTGGTAGGGTTAGGGTTAGGGT | SEQ ID NO:1 |
| Tb | TAGGGTTAGGGTTAGGGTGGTCCTGTGATCCGG | SEQ ID NO:2 |
| b' | CCGGATCACAGGACC | SEQ ID NO:3 |
| a' | CCAGGACACTAGGCC | SEQ ID NO:4 |
| TS10 | [TTAGGG]$_{10}$ | SEQ ID NO:5 |
| TS8A | [TTAGGG]$_8$TGAAGAAAATTAG | SEQ ID NO:6 |
| TS | AATCCGTCGAGCAGAGTT | SEQ ID NO:7 |
| TS1 | AATCCGTCGAGTAGGGTT | SEQ ID NO:8 |
| Ne4 | GGGGGTGGGAGCAGGGGAGG | SEQ ID NO:9 |
| c5 | [CCCTAA]$_5$ | SEQ ID NO:10 |

TABLE I-continued

| | | |
|---|---|---|
| C6 | [CCCTAA]$_6$ | SEQ ID NO:11 |
| MS2 | CGAAGTCGACTGCAGCGTACCCTGATGGTGTACG | SEQ ID NO:12 |
| Tel2 | [GGTTAG]$_3$ | SEQ ID NO:13 |
| Tel3 | [GGTTAG]$_4$ | SEQ ID NO:14 |
| Tel3m | [TTTGGG]$_4$ | SEQ ID NO:15 |

EXAMPLE 2
Production of Recombinant Proteins

Recombinant A1, UP1 and protein derivatives were expressed in *E. coli* BL21 or DH5α. Cells were grown 2–3 hrs at 37° C. until an O.D. between 0.5–2.0 at 600 nm. Induction with 100 μM IPTG was performed for 4 hr. Cells were washed with PBS and resuspended in 5 ml of PBS per 100 ml of culture to which was added 10 μl of PMSF 0.5M and 25 μl of DTT 1M. Cells were sonicated 30 sec and left on ice for 30 sec on ice. This cycle was repeated another 3 times. Triton X-100 was added to a final concentration of 1% and the mixture incubated 30 min at room temperature on a nutator. Following centrifugation for 10 min at 10,000 rpm at 4° C., 250 μl of glutathione-Sephadex (from a 50% slurry in PBS) was added to the supernatant. The mixture was incubated 30 min at 4° C., spun and washed five times with PBS. GST-A1 was eluted with 500 μl of 20 mM glutathione reduced, 200 mM Tris-HCl (pH 9.5) and 120 mM NaCl. GST-UP1 was eluted with 500 μl of 20 mM glutathione reduced, 200 mM Tris-HCl pH 7.5 and 120 mM NaCl.

To obtain proteins devoid of the GST moiety, bound proteins were treated with thrombin and the released proteins were collected. The concentration of proteins was determined by Bradford staining or by staining gels containing BSA standards.

EXAMPLE 3
Binding and Protection Assays

5'-radiolabeled oligonucleotides were incubated 30 min at 30° C. with various amounts of proteins in 10 μl final volume of 10 mM Hepes (pH 7.6), 0.1 mM EDTA, 2.5 mM MgCl$_2$, 75 mM KCl, 1 mM DTT, 0.1 μg poly (dIdC).(dIdC). Samples were loaded onto a 5% non-denaturing polyacrylamide gel (115 volts) and complexes were visualized by autoradiography. These assays have been described previously (see LaBranche et al., 1998, supra; Dallaire et al., 2000, J. Biol. Chem. in press). DNase I, exonuclease I and Bal31 protection assays were set up with 5' labeled oligonucleotides incubated with recombinant proteins in the binding buffer described above. Following a 30 min incubation at 30° C., each sample was split into two sets. One set was tested for binding in a native gel, as above. Nuclease was added to the other set (5 units of DNase I, 1 unit of exonuclease I or 1 unit of Bal31) and the mixtures were incubated 10 min at room temperature (DNase I), 1 min at 37° C. (exonuclease I) or 10 min at 30° C. (Bal31).

EXAMPLE 4
Telomerase Assay

Ten pmoles of oligonucleotides were added to proteins (G-UP1, G-A1, UP1, G-UP1Δ1, G-UP1Δ2, gp32), 1 μl [α-$^{32}$P]dGTP (3000 Ci/mmol; Amersham) and 5 μl of Telomix B (200 mM Tris-HCl [pH 8.2], 20 mM dATP, 20 mM dTTP, 4 μM dGTP, 4 mM MgCl$_2$, 8 mM EGTA, 8 mM DTT, 1 μl RNAguard, 4 mM spermidine, 0.4 mM spermine) to a final volume of 10 μl. Ten μl of HeLa S100 extract was added and the mixture was incubated 1 hr at 30° C. The reaction was stopped by the addition of 25 μl RNase mix (20 mM EDTA, 10 mM Tris-HCl [pH 7.4], 0.1 mg/ml RNase A) and incubation for 15 min at 37° C. After treatment with proteinase K (10 mM Tris-HCl [pH 7.41], 0.5% SDS, 0.3 mg/ml proteinase K for 25 μl per reaction), extension products were purified by two phenol-chloroform extractions and ethanol precipitation. Products, were fractionated onto 8% polyacrylamide/7M urea gel. To test whether the effect of UP1 can be observed after telomerase loading onto the template, the reaction was incubated in telomix B lacking dNTPs for 10 min at 30° C. without UP1. dNTPs were then added to start elongation by telomerase with or without the addition of UP1 and the mixture was incubated at 30° C. for an additional 1 hr. In competition experiments, TS8A or MS2 oligonucleotides were incubated with UP1 for 15 min at 25° C. S100 extract was then added and incubated for another 15 min at room temperature. Lastly, template oligonucleotides, [α-$^{32}$P]dGTP and Telomix B were added to the mixture. To test RNA-dependent elongation, RNase A (final concentration: 0.25 mg/ml) was added to the S100 extract before incubation with TS10.

EXAMPLE 5
TdT Assay

The assay was performed essentially as described by Froelich-Ammon et al. (13). 0.83 pmole of oligonucleotides (TS10 or TS) were added to UP1 or gp32 protein in 1×TdT buffer. The mixture was incubated overnight at 4° C. or 1 hr at 30° C. TdT (5U) and 0.5 μl of dTTP (400 Ci/mmol; Amersham) were added to a final volume of 40 μl and incubated for one hour at 37° C. The reaction was stopped by incubation for 2 hrs at 45° C. in 200 μl of stop solution (10 mM Tris-HCl [pH 7.5], 15 mM EDTA, 0.6% SDS, and 0.1 mg/ml proteinase K). Labeled extension products were purified by two extractions with phenol-chloroform and ethanol precipitation, and were fractionated onto a 8% polyacrylamide/7 M urea gel.

EXAMPLE 6
Lagging-strand Synthesis Assay

The procedure described by Reveal et al. (Reveal et al., 1997, J Biol Chem 272:11678) was used. HeLa nuclear extract, HeLa S100 and CB3 nuclear extract were prepared and dialyzed in 10 mM Tris-HCl (pH 7.5), 5 mM MgCl$_2$, 7.5 mM DTT. Essentially, 5 pmoles of TS10 oligonucleotide was incubated in 10 mM Tris-HCl (pH 7.5), 5 mM MgCl$_2$, 7.5 mM DTT with 1 mM each of rATP, rCTP, rUTP, dATP and dTTP, 10 μM dCTP, 100 nM of [α-$^{32}$P]dCTP (3 μCi; Amersham) and 1 μl of HeLa nuclear extract for 1 hr at 37° C. The reaction was stopped by the addition of 100 mM EDTA and the products were purified by phenol-chloroform extraction and ethanol precipitation. Reaction products were loaded onto a 20% polyacrylamide/7 M urea gel and revealed by autoradiography. When exogenous proteins were added to the assay, they were incubated with TS10, dNTPs and [α-$^{32}$P]dCTP for 30 minutes at 30° C. before the addition of rNTPs and the nuclear extract. CB3 nuclear extract and HeLa post-cytoplasmic S100 extract were also used, but without pre-dialysis of the extracts. For competition experiments, the TS10/protein mixture was co-incubated with the indicated amounts of Tel2, Ne4 or TS10 oligonucleotides.

EXAMPLE 7
RNA Binding Assays of A1/UP1 Based on the Formation of a Complex Separated by Gel-migration RNA mobility-shift assays are performed by incubating RNAs for 15 minutes on ice prior to addition of 1 mg/ml heparin and incubation for 2 min on ice. The reactions are run on a 5% native acrylamide gel (29:1 acrylamide:bis-acrylamide, 5% glycerol, 50 mM Tris [pH 8.8], 50 mM glycine) in Tris-glycine running buffer (50 mM Tris [pH 8.8], 50 mM glycine). The gel is dried and exposed on film before binding efficiency is measured. These assays have been described previously for a number of RNA binding proteins (Blanchette and Chabot 1999, EMBO J.18:1939).

EXAMPLE 8
Binding Assays of A1/UP1 Based on Nitrocellulose Binding

In a 96-well microtiter plate, 25 μl (1 μM) of recombinant A1/UP1 protein is loaded in each well. To the protein solution, 25 μl of 5 nM of $^{32}$P-RNA or $^{32}$P-DNA are added and the plate is incubated for 10 minutes at 30° C. 40 μl of the protein-RNA solution are filtered through a Hybond-N membrane (Amersham-Pharmacia Biotech) using a 96-well dot-blot apparatus and washed 3 times with 100 μl of washing buffer (50% D-Buffer, 3.2 mM MgCl$_2$) pre-warmed at 30° C. The filter is then exposed in a cassette for PhosphorImager to measure the amount of radioactivity which was bound. Similar assays has been described previously (Mayeda et al. 1994, 13:5483) and are based on the fact that proteins bind to nitrocellulose while nucleic acid do not unless they are bound by proteins.

EXAMPLE 9
Protein Expression and Purification for Assessing A1/UP1 Binding to Telomorase Procedure I to purify rA1 and rUP1 has been described previously in LaBranche et al. (1998). Purification of rA1 and rUP1 by Procedure II was as follows. The expression plasmids encoding rA1 or rUP1 were transformed in *E. coli* B21 strains and incubated overnight in 25 ml of L-broth media containing 100 μg/μl of ampicilline. Ten ml of this culture was then transferred to 500 ml of L-broth/ampicilline. The protein induction was realized by addition of IPTG to a final concentration of 100 μM when the culture reached 0.6–2.0 OD$_{600}$. After 4 hours of induction, the culture was centrifuged at 3500 rpm at 4° C. for 10 minutes. The supernatant was then removed and the pellet washed and resuspended in washing buffer [50 mM piperazine (pH 9.8), 0.5 M NaCl, 1 mM EDTA and 1 mM DTT]. Cells were spinned at 10K/4° C. for 10 min. The pellet was resuspended in lysis buffer [washing buffer with 0.3 mg/ml of lysozyme, 0.5 mM PMSF, 1.6 mM benzamidine and 2 μM bacitracine]. The resuspended pellet was sonicated 4×30 sec. Triton-X100 was then added to a final concentration of 1% and the solution was incubated on a rotator at 4° C. for 30 min. The mixture was centrifuged at 4° C. for 10 min at 10 000 rpm. The pellet was washed, centrifuged again and resuspended in washing buffer. 500 μl of gluthatione-sepharose beads were then added to the solution and incubated for one hour at 4° C. Beads were then recovered and elution of rA1 and rUP1 was performed in washing buffer containing 200 mM piperazine and 20 mM gluthatione reduced. This last step was repeated 3 times. The eluates were pooled and dialysed against buffer DN [20 mM Hepes pH 7.9, 100 mM KCl, 5% glycerol, 0.2 mM EDTA, 0.5 mM PMSF, 0.5 mM DTT and 0.1% NP-40].

EXAMPLE 10
Binding Assay on Agarose Adipic Acid Hydrazide Columns 0.01 μM of telomeric oligonucleotide TS10 was purified on a 10% denaturing acylamide gel [38:2 acrylamide/bis-acrylamide, 20% formamide, 8 M Urea, 90 mM Tris-borate and 2 mM EDTA]. The purified oligonucleotide was resuspended in water and coupled to 250 μl of agarose adipic hydrazide according to the manufacturer's recommandation (Pharmacia Biotech). Agarose beads coupled with TS10 were packed in a 200 μl pipetman tip. Each sample was mixed in buffer DN [20 mM Hepes pH 7.9, 100 mM KCl, 5% Glycerol, 0.2 mM EDTA, 0.5 mM PMSF, 0.5 mM DTT and 0.1% NP 40] and was then applied to the column. Each column was washed with buffer DN. Stepwise elutions were accomplished with 200 μl of buffer DN containing increasing salt concentration as indicated. Input, flow-through and eluted fractions were processed in two steps. First, the protein profile was monitored by silver staining after fractionation by SDS-PAGE. Second, RNA was extracted with phenol/chloroform/isoamylalcohol, ethanol precipitated and fractionated on a 5% acrylamide-8 M urea gel.

Although the present invention has been described hereinabove by way of preferred embodiments thereof, it can be modified, without departing from the spirit and nature of the subject invention as defined in the appended claims.

---

What is claimed is:

1. A method of identifying an agent which modulates telomere biogenesis in vitro comprising:
    (a) incubating a single-stranded nucleic acid target sequence for A1/UP1, wherein said target nucleic acid sequence is selected from telomerase RNA and telomeric DNA, together with A1/UP1, a fragment thereof, or recombinant A1/UP1, wherein said fragment thereof or recombinant A1/UP1 comprises a portion of at least one of RRM1 and RRM2 of hnRNP A1 which enables said fragment or recombinant A1/UP1 to bind to single-stranded telomeric DNA and/or telomerase RNA; and
    (b) determining at least one of a binding between said A1/UP1, fragment thereof, or recombinant A1/UP1 and said target nucleic acid sequence and an enzymatic activity dependent on the binding between said A1/UP1, fragment thereof, or recombinant A1/UP1 and said target nucleic acid sequence;
    wherein said agent is identified as a modulator of telomere biogenesis when said binding of A1/UP1, fragment thereof, or recombinant A1/UP1 or said enzymatic activity is measurably different in the presence of said agent, as compared to in the absence thereof.

2. The method of claim 1, wherein said nucleic acid target sequence is telomeric single-stranded G-rich DNA.

3. The method of claim 2, wherein binding between said A1/UP1, fragment thereof or recombinant A1/UP1 and said telomeric single-stranded G-rich DNA is determined.

4. The method of claim 3, wherein said binding is determined by gel shift assay.

5. The method of claim 2, wherein a binding between said telomeric single-stranded G-rich DNA sequence and said A1/UP1, fragment thereof or recombinant A1/UP1 is indirectly measured using a nuclease assay.

6. The method of claim 2, wherein a binding between said telomeric single-stranded G-rich DNA sequence and said A1/UP1, fragment thereof or recombinant A1/UP1 is indirectly measured using a telomerase extension assay.

7. The method of claim 2, wherein a binding between said telomeric single-stranded G-rich DNA sequence and said A1/UP1, fragment thereof or recombinant A1/UP1 is indirectly measured using a terminal nucleotidyl transferase (TdT) elongation assay.

8. The method of claim 2, wherein a binding between said telomeric single-stranded G-rich DNA sequence and said A1/UP1, fragment thereof or recombinant A1/UP1 is indirectly measured using a rNTP-dependent DNA polymerase assay.

9. The method of claim 1, wherein said nucleic acid target sequence is telomerase RNA.

10. The method of claim 9, wherein a binding between said telomerase RNA sequence and said A1/UP1, fragment thereof or recombinant A1/UP1 is determined using a gel shift assay.

11. The method of claim 9, wherein a binding between said telomerase RNA sequence and said A1/UP1, fragment thereof or recombinant A1/UP1 is determined using a nitrocellulose binding assay.

12. A method of identifying an agent which modulates telomere biogenesis comprising: determining a formation of a ternary complex made up of:

(a) a telomeric single-stranded DNA sequence;

(b) A1/UP1, or fragment thereof, or recombinant A1/UP1 wherein said fragment or recombinant A1/UP1 comprises a portion of at least one of RRM1 and RRM2 of hnRNP A1 which enables said fragment or recombinant A1/UP1 to bind to single-stranded telomeric DNA and/or telomerase RNA; and (c) telomerase RNA, wherein a modulator of telomere biogenesis is identified when a level of said formation of said ternary complex is detectably different in the presence of said agent as compared to in the absence thereof.

13. The method of claim 2, wherein said target nucleic acid comprises at least two complete A1 binding sites.

14. The target nucleic acid of claim 13, comprising a sequence of at least 8 consecutive TAGGGT.

15. The target nucleic acid of claim 14, comprising a sequence of 9 consecutive TAGGGT.

* * * * *